United States Patent
Shimuta

(10) Patent No.: US 10,390,716 B2
(45) Date of Patent: Aug. 27, 2019

(54) PULSE TRANSMISSION TIME MEASURING APPARATUS AND BIOLOGICAL STATE ESTIMATING APPARATUS

(71) Applicant: Murata Manufacturing Co., Ltd., Nagaokakyo-shi, Kyoto-fu (JP)

(72) Inventor: Toru Shimuta, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 288 days.

(21) Appl. No.: 15/292,437

(22) Filed: Oct. 13, 2016

(65) Prior Publication Data

US 2017/0027459 A1    Feb. 2, 2017

Related U.S. Application Data

(63) Continuation of application No. PCT/JP2015/059887, filed on Mar. 30, 2015.

(30) Foreign Application Priority Data

Apr. 14, 2014  (JP) ................................. 2014-083234

(51) Int. Cl.
   *A61B 5/024* (2006.01)
   *A61B 5/0245* (2006.01)
   (Continued)

(52) U.S. Cl.
   CPC ........ *A61B 5/02433* (2013.01); *A61B 5/0245* (2013.01); *A61B 5/0261* (2013.01);
   (Continued)

(58) Field of Classification Search
   USPC ....................................................... 600/473
   See application file for complete search history.

(56) References Cited

U.S. PATENT DOCUMENTS

| 4,893,631 A | 1/1990 | Wenzel et al. |
| 6,319,205 B1 | 11/2001 | Goor et al. |

(Continued)

FOREIGN PATENT DOCUMENTS

| CN | 1228014 A | 9/1999 |
| CN | 101828908 A | 9/2010 |

(Continued)

OTHER PUBLICATIONS

Official Communication issued in Chinese Patent Application No. 201580019782.6, dated Aug. 28, 2018.

(Continued)

*Primary Examiner* — Pierre E Elisca
(74) *Attorney, Agent, or Firm* — Keating & Bennett, LLP

(57) ABSTRACT

A pulse transmission time measuring apparatus includes a first photoplethysmographic sensor that includes a first light emitter and a first light receiver and detects a first photoplethysmographic signal, and a second photoplethysmographic sensor that includes a second light emitter and a second light receiver and detects a second photoplethysmographic signal. The first and second photoplethysmographic sensors are disposed on a contact surface that comes into contact with the body when the pulse transmission time measuring apparatus is attached to the body. The spacing between the second light emitter and the second light receiver is smaller than the spacing between the first light emitter and the first light receiver. The second photoplethysmographic sensor detects the second photoplethysmographic signal corresponding to the flow of blood in the capillaries. The first photoplethysmographic sensor detects the first photoplethysmographic signal corresponding to the flow of blood in an artery located deeper than the capillaries and thicker than the capillaries.

24 Claims, 10 Drawing Sheets

(51) Int. Cl.
  *A61B 5/026* (2006.01)
  *A61B 5/00* (2006.01)
  *A61M 21/02* (2006.01)
  *A61M 21/00* (2006.01)

(52) U.S. Cl.
  CPC .......... *A61B 5/02438* (2013.01); *A61B 5/681* (2013.01); *A61B 5/7246* (2013.01); *A61B 5/7278* (2013.01); *A61B 2562/0238* (2013.01); *A61B 2562/043* (2013.01); *A61M 21/02* (2013.01); *A61M 2021/0066* (2013.01); *A61M 2205/3303* (2013.01); *A61M 2205/3306* (2013.01); *A61M 2209/088* (2013.01); *A61M 2230/06* (2013.01)

(56) References Cited

U.S. PATENT DOCUMENTS

| | | | |
|---|---|---|---|
| 2006/0200011 A1* | 9/2006 | Suzuki | A61B 5/0205 600/301 |
| 2009/0204011 A1 | 8/2009 | Suzuki | |
| 2010/0331709 A1 | 12/2010 | Matsumura et al. | |
| 2011/0054328 A1 | 3/2011 | Hyogo et al. | |
| 2018/0329060 A1* | 11/2018 | Pacala | G02B 27/0955 |
| 2019/0056497 A1* | 2/2019 | Pacala | H01L 27/14643 |
| 2019/0090737 A1* | 3/2019 | Pugh | A61B 3/113 |

FOREIGN PATENT DOCUMENTS

| | | |
|---|---|---|
| CN | 103637787 A | 3/2014 |
| JP | 02-1226 A | 1/1990 |
| JP | 04-5949 A | 1/1992 |
| JP | 05-207978 A | 8/1993 |
| JP | 09-215664 A | 8/1997 |
| JP | 10-295657 A | 11/1998 |
| JP | 2004-321253 A | 11/2004 |
| JP | 2005-040261 A | 2/2005 |
| JP | 2006-212218 A | 8/2006 |
| JP | 3988674 B2 | 10/2007 |
| JP | 2009-183628 A | 8/2009 |
| JP | 2009-189416 A | 8/2009 |
| JP | 2011-050438 A | 3/2011 |
| JP | 2011-212364 A | 10/2011 |

OTHER PUBLICATIONS

Official Communication issued in corresponding International Patent Application No. PCT/JP2015/059887, dated Apr. 21, 2015.

* cited by examiner

PULSE TRANSMISSION TIME MEASURING APPARATUS AND BIOLOGICAL STATE ESTIMATING APPARATUS

CROSS REFERENCE TO RELATED APPLICATIONS

This application claims the benefit of priority to Japanese Patent Application 2014-083234 filed Apr. 14, 2014 and is a Continuation Application of PCT/JP2015/059887 filed on Mar. 30, 2015. The entire contents of each of these applications are hereby incorporated herein by reference.

BACKGROUND OF THE INVENTION

1. Field of the Invention

The present invention relates to a pulse transmission time measuring apparatus that measures pulse transmission time, and a biological state estimating apparatus including the pulse transmission time measuring apparatus.

2. Description of the Related Art

Pulse wave velocity measuring apparatuses are known in the art to measure pulse wave velocity (or pulse transmission time) as information related to values such as the rate and time of propagation of a pulse wave in the arteries of a living body. The pulse wave velocity represents information related to the rate at which a pulse wave propagates between two areas of a living body. Thus, measurement of pulse wave velocity (or pulse transmission time) requires attaching two sensors to a living body to obtain measurements of a biological signal, such as an electrocardiographic waveform (electrocardiogram) and arterial pulse waves, at two different locations.

Japanese Unexamined Patent Application Publication No. 2004-321253 discloses a pulse wave velocity measuring apparatus that enables measurement of central pulse wave velocity and peripheral pulse wave velocity. The pulse wave velocity measuring apparatus includes the following components on its surface that is pressed toward the wrist: a semiconductor pressure-sensitive element that is pressed from above the epidermis toward the radial artery to detect radial artery pulse waves, and a piezoelectric sheet that is pressed toward the radial artery. The pulse wave velocity measuring apparatus also includes a probe attached to the fingertips to detect peripheral pulse waves. Further, the main body of a telephone includes a cardiac sound extracting unit that extracts cardiac sound from a signal output from the piezoelectric sheet, a central pulse wave velocity calculator that calculates the pulse wave velocity (central pulse wave velocity) from the heart to the wrist based on the extracted cardiac sound and the radial artery pulse waves, and a peripheral pulse wave velocity calculator that calculates the pulse wave velocity (peripheral pulse wave velocity) from the wrist to the fingertips based on the radial artery pulse waves and the peripheral pulse waves.

In the pulse wave velocity measuring apparatus, after the probe is attached to the epidermis of the fingertips, the pressing surface of a biological signal sensor unit is pressed against the wrist such that the pressure sensitive element disposed on the pressing surface presses against the radial artery, and the piezoelectric sheet disposed on the pressing surface presses against the radius. In this state, radial artery pulse waves are detected by the pressure sensitive element, vibrations including cardiac sound are detected by the piezoelectric sheet, and peripheral pulse waves are detected by the probe. The radial artery pulse waves, the cardiac sound, and the peripheral pulse waves are thus measured simultaneously. Then, the central pulse wave velocity is calculated from the cardiac sound and the radial artery pulse waves, and the peripheral pulse wave velocity is calculated from the radial artery pulse waves and the peripheral pulse waves.

Pulse wave velocity is measured as described above in the following manner by using the pulse wave velocity measuring apparatus described in Japanese Unexamined Patent Application Publication No. 2004-321253 First, the main body of the probe is attached to the fingertips, and the input terminal of the probe is inserted into the main body of the telephone. Then, with the cellular phone gripped in such a way as to touch a second electrode with one hand (for example, the right hand), the cellular phone needs to be pressed against the wrist of the other hand (for example, the left hand) such that a first pressing surface presses against the radial artery from above the epidermis and, at the same time, a second pressing surface presses against the radius from above the epidermis.

Thus, the pulse wave velocity measuring apparatus requires use of both hands to measure pulse wave velocity. This makes it difficult to obtain continuous measurement of pulse wave velocity during activities (for example, during daily life). Further, the attachment of the apparatus is cumbersome as described above, resulting in relatively poor ease of use.

SUMMARY OF THE INVENTION

Preferred embodiments of the present invention provide a pulse transmission time measuring apparatus that allows for easier attachment to the body and enables continuous measurement of pulse transmission time during activities, and a biological state estimating apparatus including the pulse transmission time measuring apparatus.

A pulse transmission time measuring apparatus according to a preferred embodiment of the present invention includes a first photoplethysmographic sensor that includes a first light emitter and a first light receiver, and detects a first photoplethysmographic signal, a second photoplethysmographic sensor that includes a second light emitter and a second light receiver, and detects a second photoplethysmographic signal, a peak detector that detects a peak of the first photoplethysmographic signal detected by the first photoplethysmographic sensor, and a peak of the second photoplethysmographic signal detected by the second photoplethysmographic sensor, and a pulse transmission time calculator that calculates a pulse transmission time from the time difference between the peak of the first photoplethysmographic signal detected by the peak detector and the peak of the second photoplethysmographic signal detected by the peak detector. The first photoplethysmographic sensor and the second photoplethysmographic sensor are disposed on a contact surface of the pulse transmission time measuring apparatus that, when the pulse transmission time measuring apparatus is attached to a body, comes into contact with the body. The second photoplethysmographic sensor detects the second photoplethysmographic signal corresponding to the flow of blood in capillaries. The first photoplethysmographic sensor detects the first photoplethysmographic signal corresponding to the flow of blood in an artery thicker than the capillaries.

In a pulse transmission time measuring apparatus according to a preferred embodiment of the present invention, the first photoplethysmographic sensor and the second photoplethysmographic sensor are disposed on a contact surface of the pulse transmission time measuring apparatus that, when the pulse transmission time measuring apparatus is attached to the body, comes into contact with the body. Thus, by simply attaching the pulse transmission time measuring apparatus to the user such that the contact surface comes into contact with the body (for example, the wrist), the second photoplethysmographic signal corresponding to the flow of blood in the capillaries, and the first photoplethysmographic signal corresponding to the flow of blood in an artery thicker than the capillaries are able to be detected. This configuration allows for easier attachment to the body, and enables continuous measurement of pulse transmission time during activities (during daily life).

A pulse transmission time measuring apparatus according to a preferred embodiment of the present invention is preferably configured so that the second light emitter and the second light receiver have a spacing that is less than the spacing between the first light emitter and the first light receiver.

In this case, the spacing between the second light emitter and the second light receiver is preferably shorter than the spacing between the first light emitter and the first light receiver. This allows the second photoplethysmographic sensor to detect the second photoplethysmographic signal corresponding to the flow of blood in the capillaries located close to the epidermis (that is, at a shallow depth). By contrast, the first photoplethysmographic sensor is able to detect the first photoplethysmographic signal corresponding to the flow of blood in an artery located distant from the epidermis (that is, at a deep depth) and thicker than the capillaries.

A pulse transmission time measuring apparatus according to a preferred embodiment of the present invention is preferably configured so that the first light emitter outputs light with a wave length of about 800 nm to about 1000 nm, and the second light emitter outputs light with a wave length of about 450 nm to about 580 nm, for example.

The blue to yellow-green wave lengths of light in the range of about 450 nm to about 580 nm are subject to strong absorption in living bodies. Thus, these wave lengths of light allow for greater output of the resulting photoplethysmographic signal but do not allow the optical path length to be extended. By contrast, near-infrared light with wave lengths in the range of about 800 nm to about 1000 nm is not subject to strong absorption in living bodies. Thus, such near-infrared light provides smaller output of the resulting photoplethysmographic signal but allows for extended optical path length. Therefore, the above-mentioned configuration allows for improved S/N compared to when sources of light of the same wave length are used as the first light emitter and the second light emitter.

A pulse transmission time measuring apparatus according to a preferred embodiment of the present invention includes a first photoplethysmographic sensor that includes a first light emitter and a first light receiver, and detects a first photoplethysmographic signal, a second photoplethysmographic sensor that includes the first light emitter and a second light receiver, and detects a second photoplethysmographic signal, a peak detector that detects a peak of the first photoplethysmographic signal detected by the first photoplethysmographic sensor, and a peak of the second photoplethysmographic signal detected by the second photoplethysmographic sensor, and a pulse transmission time calculator that calculates a pulse transmission time from the time difference between the peak of the first photoplethysmographic signal detected by the peak detector and the peak of the second photoplethysmographic signal detected by the peak detector. The first photoplethysmographic sensor and the second photoplethysmographic sensor are disposed on a contact surface of the pulse transmission time measuring apparatus that, when the pulse transmission time measuring apparatus is attached to the body, comes into contact with the body. The second photoplethysmographic sensor detects the second photoplethysmographic signal corresponding to the flow of blood in capillaries. The first photoplethysmographic sensor detects the first photoplethysmographic signal corresponding to the flow of blood in an artery thicker than the capillaries.

In a pulse transmission time measuring apparatus according to a preferred embodiment of the present invention, the first photoplethysmographic sensor and the second photoplethysmographic sensor are disposed on a contact surface of the pulse transmission time measuring apparatus that, when the pulse transmission time measuring apparatus is attached to the body, comes into contact with the body. Thus, by simply attaching the pulse transmission time measuring apparatus to the user such that the contact surface comes into contact with the body (for example, the wrist), the second photoplethysmographic signal corresponding to the flow of blood in the capillaries, and the first photoplethysmographic signal corresponding to the flow of blood in an artery thicker than the capillaries are able to be detected. This configuration allows for easier attachment to the body, and enables continuous measurement of pulse transmission time during activities (during daily life). In this case, the sharing of the same light emitter allows for, for example, reduced size, weight, and cost of the apparatus.

A pulse transmission time measuring apparatus according to a preferred embodiment of the present invention is preferably configured so that the first light emitter and the second light receiver have a spacing that is less than the spacing between the first light emitter and the first light receiver.

In this case, the spacing between the first light emitter and the second light receiver is preferably shorter than the spacing between the first light emitter and the first light receiver. This configuration allows the second photoplethysmographic sensor to detect the second photoplethysmographic signal corresponding to the flow of blood in the capillaries located close to the epidermis (that is, at a shallow depth). By contrast, the first photoplethysmographic sensor is able to detect the first photoplethysmographic signal corresponding to the flow of blood in an artery located distant from the epidermis (that is, at a deep depth) and thicker than the capillaries.

A pulse transmission time measuring apparatus according to a preferred embodiment of the present invention includes a first photoplethysmographic sensor that includes a first light emitter and a first light receiver, and detects a first photoplethysmographic signal, a second photoplethysmographic sensor that includes a second light emitter and the first light receiver, and detects a second photoplethysmographic signal, a peak detector that detects a peak of the first photoplethysmographic signal detected by the first photoplethysmographic sensor, and a peak of the second photoplethysmographic signal detected by the second photoplethysmographic sensor, and a pulse transmission time calculator that calculates a pulse transmission time from the time difference between the peak of the first photoplethysmographic signal detected by the peak detector and the peak of the second photoplethysmographic signal detected by the peak detector. The first photoplethysmographic sensor and the second photoplethysmographic sensor are disposed on a contact surface of the pulse transmission time measuring apparatus that, when the pulse transmission time measuring apparatus is attached to the body, comes into contact with the body. The second photoplethysmographic sensor detects the second photoplethysmographic signal corresponding to the flow of blood in capillaries. The first photoplethysmographic sensor detects the first photoplethysmographic signal corresponding to the flow of blood in an artery thicker than the capillaries.

In a pulse transmission time measuring apparatus according to a preferred embodiment of the present invention, the first photoplethysmographic sensor and the second photoplethysmographic sensor are disposed on a contact surface of the pulse transmission time measuring apparatus that, when the pulse transmission time measuring apparatus is attached to the body, comes into contact with the body. Thus, by simply attaching the pulse transmission time measuring apparatus to the user such that the contact surface comes into contact with the body (for example, the wrist), the second photoplethysmographic signal corresponding to the flow of blood in the capillaries, and the first photoplethysmographic signal corresponding to the flow of blood in an artery thicker than the capillaries are able to be detected. This configuration allows for easier attachment to the body, and enables continuous measurement of pulse transmission time during activities (during daily life). In this case, the sharing of the same light receiver allows for, for example, reduced size, weight, and cost of the apparatus.

A pulse transmission time measuring apparatus according to a preferred embodiment of the present invention is preferably configured so that the second light emitter and the first light receiver have a spacing that is less than the spacing between the first light emitter and the first light receiver.

In this case, the spacing between the second light emitter and the first light receiver is preferably shorter than the spacing between the first light emitter and the first light receiver. This configuration allows the second photoplethysmographic sensor to detect the second photoplethysmographic signal corresponding to the flow of blood in the capillaries located close to the epidermis (that is, at a shallow depth). By contrast, the first photoplethysmographic sensor is able to detect the first photoplethysmographic signal corresponding to the flow of blood in an artery located distant from the epidermis (that is, at a deep depth) and thicker than the capillaries.

A pulse transmission time measuring apparatus according to a preferred embodiment of the present invention is preferably configured so that the first light emitter outputs light with a wave length of about 800 nm to about 1000 nm, and the second light emitter outputs light with a wave length of about 450 nm to about 580 nm.

This configuration allows for improved S/N compared to when sources of light of the same wave length are used as the first light emitter and the second light emitter.

A pulse transmission time measuring apparatus according to a preferred embodiment of the present invention is preferably configured so that the peak detector determines that an error condition exists if the first photoplethysmographic signal has an amplitude equal to or less than a predetermined value.

Detection of a photoplethysmographic signal at an artery located distant from the epidermis (that is, at a deep depth) and thicker than the capillaries is subject to high dependency on the detecting location. That is, displacement of the detecting location from that suitable for detection may make it impossible to properly detect a photoplethysmographic signal. In this case, if the amplitude of the first photoplethysmographic signal is equal to or less than a predetermined value, this is determined to be an error, thus allowing displacement of the detecting location to be recognized. This makes it possible to prevent measurements from being taken with such displacement of the detecting location left as it is.

A pulse transmission time measuring apparatus according to a preferred embodiment of the present invention is preferably configured so that the first photoplethysmographic sensor is capable of being varied in location.

This configuration allows the detecting location of the first photoplethysmographic sensor to be adjusted without detaching the apparatus from the body.

A pulse transmission time measuring apparatus according to a preferred embodiment of the present invention is preferably configured so that the first photoplethysmographic sensor and the second photoplethysmographic sensor are disposed on a contact surface of the pulse transmission time measuring apparatus that comes into contact with the wrist when the pulse transmission time measuring apparatus is attached to the body, and the first photoplethysmographic sensor detects the first photoplethysmographic signal corresponding to the flow of blood in the radial artery.

Among various arteries, which are thick, the radial artery in particular is located at a relatively shallow depth from the epidermis. For this reason, the above-mentioned configuration ensures stable measurement of the first photoplethysmographic signal. Furthermore, the apparatus is attached at the wrist, thus creating relatively less user resistance to attachment of the apparatus. This allows the apparatus to be attached on the user's body for an extended period of time without giving a sense of discomfort.

A pulse transmission time measuring apparatus according to a preferred embodiment of the present invention is preferably configured so that the first photoplethysmographic sensor is disposed on the contact surface such that when the pulse transmission time measuring apparatus is attached to the body, the first photoplethysmographic sensor comes into contact with an area of the epidermis over the radial artery.

This configuration allows for easy positioning of the first photoplethysmographic sensor even when the user is unable to accurately identify where the radial artery is located.

A pulse transmission time measuring apparatus according to a preferred embodiment of the present invention is preferably configured so that an area of the contact surface where the first photoplethysmographic sensor is disposed has a shape that, when the pulse transmission time measuring apparatus is attached to the body, protrudes in a convex manner toward the wrist relative to an area of the contact surface where the first photoplethysmographic sensor is not disposed.

The radial artery is located deeper from the epidermis than the capillaries. In this case, the area where the first photoplethysmographic sensor is disposed protrudes in a convex shape toward the wrist. This configuration allows the first photoplethysmographic sensor to be pressed toward the wrist to ensure more stable measurement of the first photoplethysmographic signal.

A pulse transmission time measuring apparatus according to a preferred embodiment of the present invention includes a photoplethysmographic sensor that includes a light emitter and a light receiver, and detects a photoplethysmographic signal, a piezoelectric pulse wave sensor that includes a piezoelectric element and detects a piezoelectric pulse wave signal, a peak detector that detects a peak of the photoplethysmographic signal detected by the photoplethysmographic sensor, and a peak of the piezoelectric pulse wave signal detected by the piezoelectric pulse wave sensor, and a pulse transmission time calculator that calculates a pulse transmission time from the time difference between the peak of the photoplethysmographic signal detected by the peak detector and the peak of the piezoelectric pulse wave signal detected by the peak detector. The photoplethysmographic sensor and the piezoelectric pulse wave sensor are disposed on a contact surface of the pulse transmission time measuring apparatus that, when the pulse transmission time measuring apparatus is attached to the body, comes into contact with the body. The photoplethysmographic sensor detects the photoplethysmographic signal corresponding to the flow of blood in capillaries. The piezoelectric pulse wave sensor detects the piezoelectric pulse wave signal corresponding to the flow of blood in an artery thicker than the capillaries.

In a pulse transmission time measuring apparatus according to a preferred embodiment of the present invention, the first photoplethysmographic sensor and the piezoelectric pulse wave sensor are disposed on a contact surface of the pulse transmission time measuring apparatus that, when the pulse transmission time measuring apparatus is attached to the body, comes into contact with the body. Thus, by simply attaching the pulse transmission time measuring apparatus to the user such that the contact surface comes into contact with the body (for example, the wrist), the photoplethysmographic signal corresponding to the flow of blood in the capillaries, and the piezoelectric pulse wave signal corresponding to the flow of blood (pulsation) in an artery thicker than the capillaries are able to be detected. This configuration allows for easier attachment to the body, and enables continuous measurement of pulse transmission time during activities (during daily life).

A pulse transmission time measuring apparatus according to a preferred embodiment of the present invention is preferably configured so that the peak detector determines that an error condition exists if the piezoelectric pulse wave signal has an amplitude equal to or less than a predetermined value.

As described above, detection of a piezoelectric pulse wave signal at an artery located distant from the epidermis (that is, at a deep depth) and thicker than the capillaries is subject to high dependency on the detecting location. That is, displacement of the detecting location from that suitable for detection may make it impossible to properly detect a piezoelectric pulse wave signal. In this case, if the amplitude of the piezoelectric pulse wave signal is equal to or less than a predetermined value, this is determined to be an error, thus allowing displacement of the detecting location to be recognized. This makes it possible to prevent measurements from being taken with such displacement of the detecting location left as it is.

A pulse transmission time measuring apparatus according to a preferred embodiment of the present invention is preferably configured so that the piezoelectric pulse wave sensor is capable of being varied in location.

This configuration allows the detecting location of the piezoelectric pulse wave sensor to be adjusted without detaching the apparatus from the body.

A pulse transmission time measuring apparatus according to a preferred embodiment of the present invention is preferably configured so that the photoplethysmographic sensor and the piezoelectric pulse wave sensor are disposed on a contact surface of the pulse transmission time measuring apparatus that comes into contact with the wrist when the pulse transmission time measuring apparatus is attached to the body, and the piezoelectric pulse wave sensor detects the piezoelectric pulse wave signal corresponding to the flow of blood in the radial artery.

As described above, among various arteries that are thick, the radial artery in particular is located at a relatively shallow depth from the epidermis. For this reason, the above-mentioned configuration ensures stable measurement of the piezoelectric pulse wave signal. Furthermore, the apparatus is attached at the wrist, thus creating relatively less user resistance to attachment of the apparatus. This allows the apparatus to be attached on the user's body for an extended period of time without giving a sense of discomfort.

A pulse transmission time measuring apparatus according to a preferred embodiment of the present invention is preferably configured so that the piezoelectric pulse wave sensor is disposed on the contact surface such that when the pulse transmission time measuring apparatus is attached to the body, the piezoelectric pulse wave sensor comes into contact with an area of the epidermis over the radial artery.

This configuration allows for easy positioning of the piezoelectric pulse wave sensor even when the user is unable to accurately identify where the radial artery is located.

A pulse transmission time measuring apparatus according to a preferred embodiment of the present invention is preferably configured so that an area of the contact surface where the piezoelectric pulse wave sensor is disposed has a shape that, when the pulse transmission time measuring apparatus is attached to the body, protrudes in a convex manner toward the wrist relative to an area of the contact surface where the piezoelectric pulse wave sensor is not disposed.

As described above, the radial artery is located deeper from the epidermis than the capillaries. In this regard, the area where the piezoelectric pulse wave sensor is disposed protrudes in a convex shape toward the wrist, and the piezoelectric pulse wave sensor is thus pressed toward the wrist to ensure more stable measurement of the piezoelectric pulse wave signal.

A pulse transmission time measuring apparatus according to a preferred embodiment of the present invention is preferably configured so that the pulse transmission time calculator determines that an error condition exists if the pulse transmission time calculated by the pulse transmission time calculator is equal to or less than a predetermined value.

This makes it possible to easily and properly discriminate noise superimposed on the pulse wave signal, for example, noise resulting from body movements.

A biological state estimating apparatus according to a preferred embodiment of the present invention includes the pulse transmission time measuring apparatus according to any one of the preferred embodiments of the present invention described above, a pulse interval change rate acquirer that acquires the rate of change in pulse interval, and a pulse rhythm abnormality detector that determines a pulse rhythm abnormality based on the variability of the rate of change in pulse interval acquired by the pulse interval change rate acquirer.

A biological state estimating apparatus according to a preferred embodiment of the present invention makes it possible to easily and properly determinate a pulse rhythm abnormality due to arrhythmia or other causes. In this case, in particular, the biological state estimating apparatus includes the pulse transmission time measuring apparatus according to any one of the preferred embodiments of the present invention described above. This allows for easier attachment to the body, and also enables continuous detection of a pulse rhythm abnormality during activities (during daily life). Further, the variability of rate of change in pulse interval is used to enable discrimination from cyclic pulse interval variation such as respiratory variation. Further, the noise determination mentioned above may be used in combination to reduce erroneous determination of a pulse rhythm abnormality as noise such as body movement noise, thus enabling accurate determination of a pulse rhythm abnormality.

A biological state estimating apparatus according to a preferred embodiment of the present invention includes the pulse transmission time measuring apparatus according to any one of the preferred embodiments of the present invention described above, and a sleep state detector that determines that the body is not in a state suitable for sleep if the pulse transmission time calculated by the pulse transmission time calculator is equal to or less than a predetermined threshold.

A biological state estimating apparatus according to a preferred embodiment of the present invention determines that the body is not in a state suitable for sleep if the pulse transmission time is equal to or less than a predetermined threshold. It is thus possible to determine whether the user's body is in a state suitable for sleep. In particular, in this case, the biological state estimating apparatus includes the pulse transmission time measuring apparatus according to any one of the preferred embodiments of the present invention described above, thus allowing for easier attachment to the body.

A biological state estimating apparatus according to a preferred embodiment of the present invention is preferably configured to further include a forearm heater that, if it is determined by the sleep state detector that the body is not in a state suitable for sleep, raises the temperature of the forearm.

When one's fingers are cold and peripheral blood vessels are constricted, it is difficult to get to sleep (fall asleep) smoothly, and obtain deep sleep. Accordingly, a biological state estimating apparatus according to a preferred embodiment of the present invention causes the temperature of the user's forearm to rise if the user's body is not in a state suitable for sleep. This allows only the forearm to be heated without raising the temperature of the trunk of the body. This puts the user's body in a state in which the forearm is heated to cause the peripheral blood vessels in the fingers to widen, with the temperature of the trunk of the body remaining low, in other words, a state suitable for sleep. It is thus possible for the user to smoothly get to sleep (fall asleep) and obtain deep sleep.

A biological state estimating apparatus according to a preferred embodiment of the present invention includes the pulse transmission time measuring apparatus according to any one of the preferred embodiments of the present invention described above, a correlation information storage that stores autonomic function correlation information, the autonomic function correlation information being defined in advance based on the relationship between pulse transmission time and autonomic function, a biological state estimator that estimates the autonomic function of a user based on the pulse transmission time calculated by the pulse transmission time calculator, and the autonomic function correlation information stored in the correlation information storage.

A biological state estimating apparatus according to a preferred embodiment of the present invention stores the autonomic function correlation information defined in advance based on the relationship between pulse transmission time and autonomic function. Thus, by measuring the pulse transmission time of the user, and using the measured pulse transmission time as an index, autonomic function as an example of biological state is able to be estimated for evaluation. In particular, the time difference between the respective peaks of pulse waves obtained from the thick artery and the capillaries is measured. This allows the influence of the capillaries to be strongly reflected, thus enabling estimation of autonomic activities, coldness of the hand/blood circulation, and other conditions related to the constriction/dilation of blood vessels. Further, in this case, the biological state estimating apparatus includes the pulse transmission time measuring apparatus according to any one of the preferred embodiments of the present invention described above. This allows for easier attachment to the body, and also enables continuous estimation and evaluation of autonomic function during activities (during daily life).

Various preferred embodiments of the present invention allow for easier attachment to the body, and enable continuous measurement of pulse transmission time during activities (during daily life).

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described in detail with reference to the figures. In the figures, portions identical or corresponding to each other are denoted by the same reference signs. In the figures, identical elements are denoted by the same reference signs to avoid repetitive description.

Figure 1:
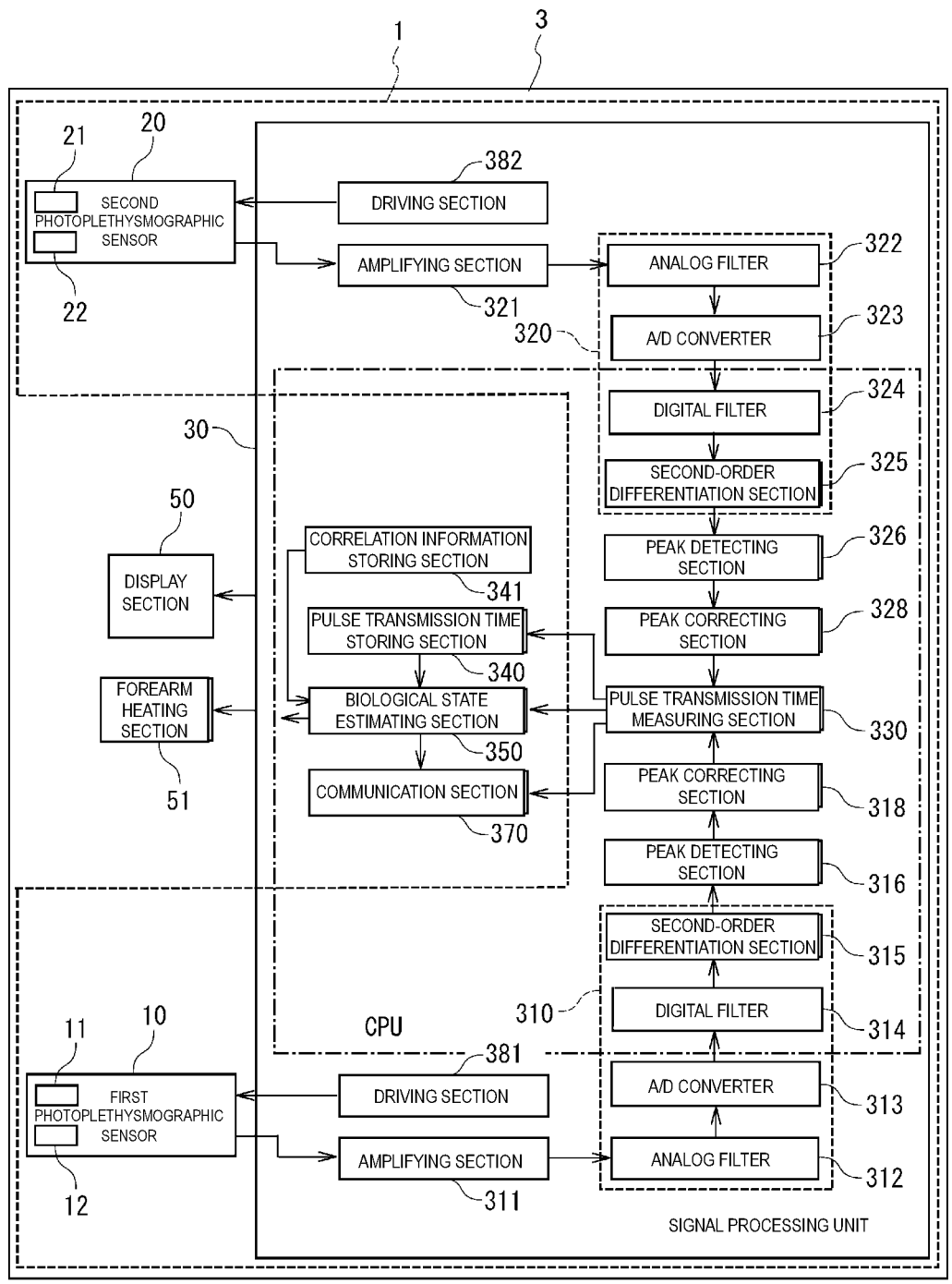
FIG. 1 is a block diagram illustrating the configuration of a biological state estimating apparatus including a pulse transmission time measuring apparatus according to a preferred embodiment of the present invention.
Figure 2:
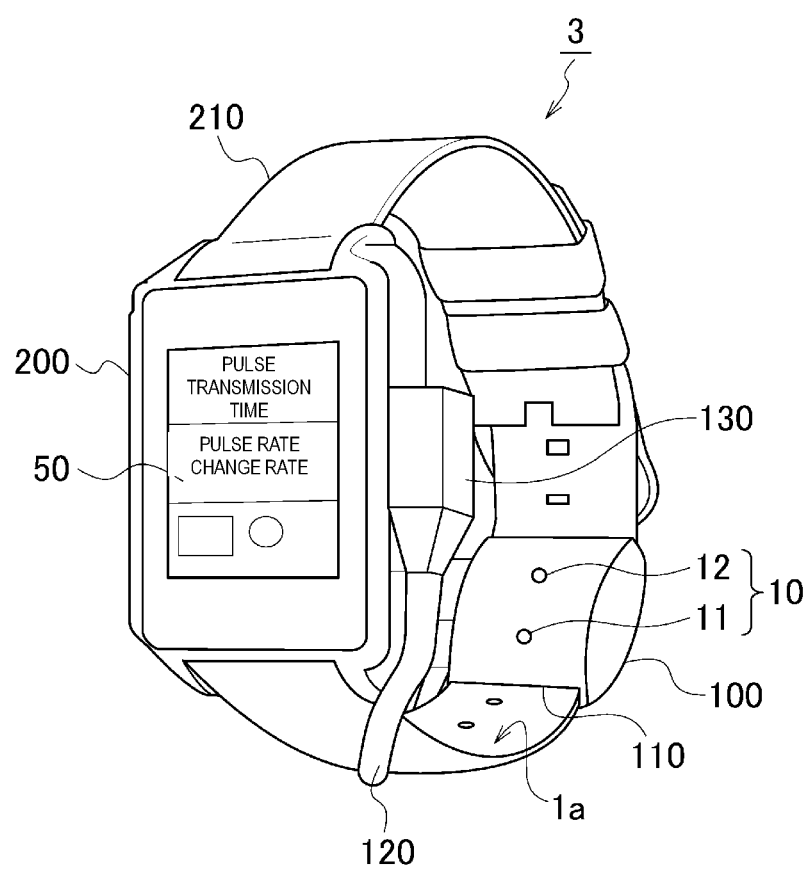
FIG. 2 illustrates the outward appearance of a wristwatch-type biological state estimating apparatus including a pulse transmission time measuring apparatus according to a preferred embodiment of the present invention.

First, the configuration of a biological state estimating apparatus 3 including a pulse transmission time measuring apparatus 1 according to a preferred embodiment of the present invention will be described with reference to FIGS. 1 and 2. FIG. 1 is a block diagram illustrating the configuration of the biological state estimating apparatus 3 including the pulse transmission time measuring apparatus 1. FIG. 2 illustrates the outward appearance of the biological state estimating apparatus 3 of a wristwatch type that includes the pulse transmission time measuring apparatus 1.

The biological state estimating apparatus 3 includes the pulse transmission time measuring apparatus 1 that detects a first photoplethysmographic signal and a second photoplethysmographic signal, and measures pulse transmission time from the time difference between the respective peaks of the detected first and second photoplethysmographic signals. Then, the biological state estimating apparatus 3 estimates the biological state (for example, pulse rhythm abnormality (arrhythmia), autonomic function, or sleep state) of the user based on the measured pulse transmission time.

To this end, the biological state estimating apparatus 3 includes a first photoplethysmographic sensor 10 that detects the first photoplethysmographic signal, a second photoplethysmographic sensor 20 that detects the second photoplethysmographic signal, and a signal processor 30 that measures pulse transmission time or other values based on the detected first and second photoplethysmographic signals, and estimates biological state. That is, the signal processor 30 is shared by the pulse transmission time measuring apparatus 1 and the biological state estimating apparatus 3. Hereinafter, these individual components will be described in detail.

The first photoplethysmographic sensor 10 is a sensor that exploits the light-absorption characteristics of hemoglobin in the blood to optically detect the first photoplethysmographic signal. Accordingly, the first photoplethysmographic sensor 10 includes a first light emitter 11 and a first light receiver 12.

Likewise, the second photoplethysmographic sensor 20 is a sensor that exploits the light-absorption characteristics of hemoglobin in the blood to optically detect the second photoplethysmographic signal. Accordingly, the second photoplethysmographic sensor 20 includes a second light emitter 21 and a second light receiver 22.

The first light emitter 11 emits light in response to a pulsed drive signal output from a driver 381 of the signal processor 30. As the first light emitter 11, for example, an LED, a vertical cavity surface emitting laser (VCSEL), or a resonant-type LED may be used. The driver 381 generates and outputs a pulsed drive signal to drive the first light emitter 11.

The first light receiver 12 outputs a detection signal corresponding to the intensity of light emitted from the first light emitter 11 and made incident on the first light receiver 12 after passing through the human body, for example, the wrist. As the first light receiver 12, for example, a photodiode or a phototransistor is suitably used. In the present preferred embodiment, a photodiode is preferably used as the first light receiver 12. The first light receiver 12 is connected to the signal processor 30. A detection signal (first photoplethysmographic signal) obtained by the first light receiver 12 is output to the signal processor 30.

Likewise, the second light emitter 21 emits light in response to a pulsed drive signal output from a driver 382 of the signal processor 30. As the second light emitter 21, for example, an LED, a VCSEL, or a resonant-type LED may be used. The driver 382 generates and outputs a pulsed drive signal to drive the second light emitter 21.

The second light receiver 22 outputs a detection signal corresponding to the intensity of light emitted from the second light emitter 21 and made incident on the second light receiver 22 after passing through the human body, for example, the wrist. As the second light receiver 22, for example, a photodiode or a phototransistor is suitably used. In the present preferred embodiment, a photodiode is used as the second light receiver 22. The second light receiver 22 is connected to the signal processor 30. A detection signal (second photoplethysmographic signal) obtained by the second light receiver 22 is output to the signal processor 30.

The first light emitter 11 preferably outputs near-infrared light with wave lengths ranging from about 800 nm to about 1000 nm. The first light emitter 11 used in the preferred embodiment outputs near-infrared light with a wave length of about 850 nm, for example. By contrast, the second light emitter 21 preferably outputs light in the blue to yellow-green wave lengths ranging from about 450 nm to about 580 nm, for example. The first light emitter 11 used in the preferred embodiment outputs green light with a wave length of about 525 nm, for example. The spacing between the second light emitter 21 and the second light receiver 22 is set less than the spacing between the first light emitter 11 and the first light receiver 12.

Blue to yellow-green wave lengths of light are subject to large absorption in living bodies, and thus the magnitude of the resulting photoplethysmographic signal is also large. However, these wave lengths of light immediately decay within living bodies, making it impossible to obtain extended optical path lengths. By contrast, near-infrared light is not subject to very large absorption in living bodies, and although the magnitude of the resulting photoplethysmographic signal is thus not very large, extended optical path lengths are able to be obtained. For these reasons, although it is possible to measure the first photoplethysmographic signal and the second photoplethysmographic signal by using the same wave length of light, it is preferred to use near-infrared light for the first photoplethysmographic sensor 10 with a large optical path length, and use blue to yellow-green wave lengths of light for the second photoplethysmographic sensor 20 with a small optical path length.

Examples of suitable methods for isolating the first photoplethysmographic signal and the second photoplethysmographic signal from each other include those based on time division (causing detected beams of light to be emitted in a pulsed fashion and shifting the timing of their emissions relative to each other), those based on wave length division (disposing a wave filter corresponding to each individual wave length in front of the light receiver), and those based on space division (spacing the detected beams of light apart to avoid their mutual interference).

Figure 3:
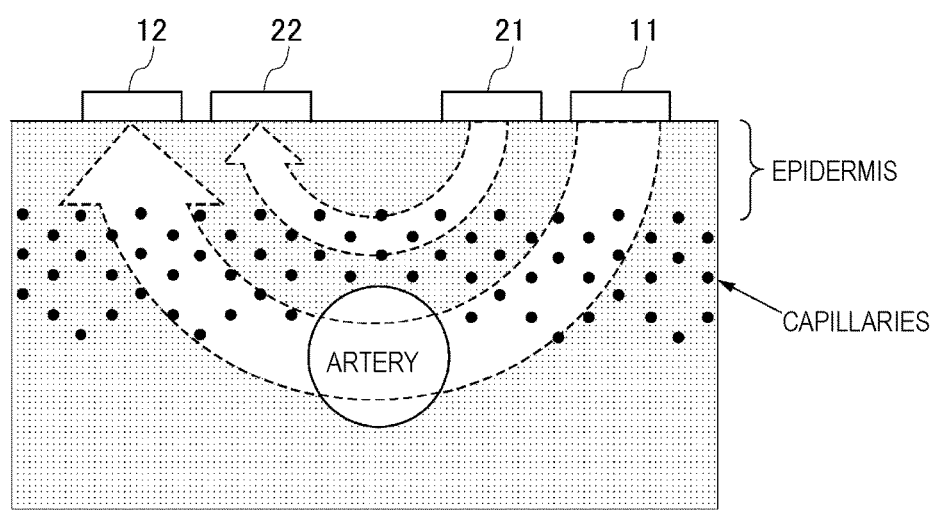
FIG. 3 illustrates the relationship between optical path lengths, and the artery in which to measure a photoplethysmographic signal.

As a result of the configuration mentioned above, the second photoplethysmographic sensor 20 with a small optical path length detects the second photoplethysmographic signal corresponding to the flow of blood in capillaries located relatively close to (that is, at a shallow depth from)

the epidermis as illustrated in FIG. 3. By contrast, the first photoplethysmographic sensor 10 with a large optical path length detects the first photoplethysmographic signal corresponding to the flow of blood in an artery located relatively distant from the epidermis (that is, at a deep depth) and thicker than the capillaries. FIG. 3 illustrates the relationship between optical path lengths (the relative placement of the light emitters 11 and 12 and the light receivers 21 and 22), and the artery in which to detect a photoplethysmographic signal.

The first photoplethysmographic sensor 10 is preferably attached at a site where a thick artery is located relatively close to the epidermis, for example, the wrist where the radial artery is located, the neck where the carotid artery is located, the elbow where the brachial artery is located, or the temple where the superficial temporal artery is located. The following description of the preferred embodiment will be directed to a case in which the biological state estimating apparatus 3 (the pulse transmission time measuring apparatus 1) is attached at the wrist.

The outward appearance of the biological state estimating apparatus 3 (the pulse transmission time measuring apparatus 1) of a wristwatch type is illustrated in FIG. 2. The biological state estimating apparatus 3 (the pulse transmission time measuring apparatus 1) of a wristwatch type includes a main body 200, a belt 210 attached to the main body 200, and a pulse wave sensor 100 attached to the belt 210 in a movable fashion.

Components such as the signal processor 30 and batteries are accommodated inside the main body 200. The second photoplethysmographic sensor 20 is disposed on the back surface of the main body 200 (the surface that comes into contact with the wrist when the biological state estimating apparatus 3 is attached to the user's body). A display 50 is mounted on the outer surface of the main body 200. Alternatively, the second photoplethysmographic sensor 20 may be disposed on the pulse wave sensor 100.

The first photoplethysmographic sensor 10 is disposed on the inner side of the pulse wave sensor 100. That is, the first photoplethysmographic sensor 10 and the second photoplethysmographic sensor 20 are disposed on a contact surface 1a that comes into contact with the wrist when the biological state estimating apparatus 3 is attached to the body, that is, the inner surfaces of the main body 200 and the belt 210, respectively. Thus, when the user attaches the biological state estimating apparatus 3 (the pulse transmission time measuring apparatus 1) of a wristwatch type over the wrist of one hand (for example, the left hand), the first photoplethysmographic sensor 10 and the second photoplethysmographic sensor 20 come into contact with the user's wrist to measure pulse transmission time and acquire biological information.

The pulse wave sensor 100 includes a horizontally elongated belt passage hole 110 through which the belt 210 is passed. With the belt 210 passed through the belt passage hole 110, the pulse wave sensor 100 is attached to the belt 210 in a movable fashion. That is, the pulse wave sensor 100 (the first photoplethysmographic sensor 10) is of a movable type that can be changed (adjusted) in its location. A cable 120 is connected to the pulse wave sensor 100. A connector 130 is connected to the cable 120. When the connector 130 is inserted (connected) to the main body 200, the pulse wave sensor 100 (the first photoplethysmographic sensor 10) is connected to the main body 200 (the signal processor 30).

The inner side of the pulse wave sensor 100 (corresponding to an area of the contact surface 1a described in the claims where the first photoplethysmographic sensor 10 is disposed) is formed in an arcuate shape extending along the belt 210. That is, the inner surface of the pulse wave sensor 100 has a shape that, when the biological state estimating apparatus 3 is attached to the body, protrudes in a smooth convex shape toward the wrist relative to the inner peripheral surface of the belt 210 and the back surface of the main body 200 (each corresponding to an area described in the claims where the first photoplethysmographic sensor 10 is not disposed). The area of this convex portion that contacts the skin preferably is a curved surface with no corners to ensure that pain due to stress concentration is not caused to the user or an impression is not left on the skin.

Figure 4:
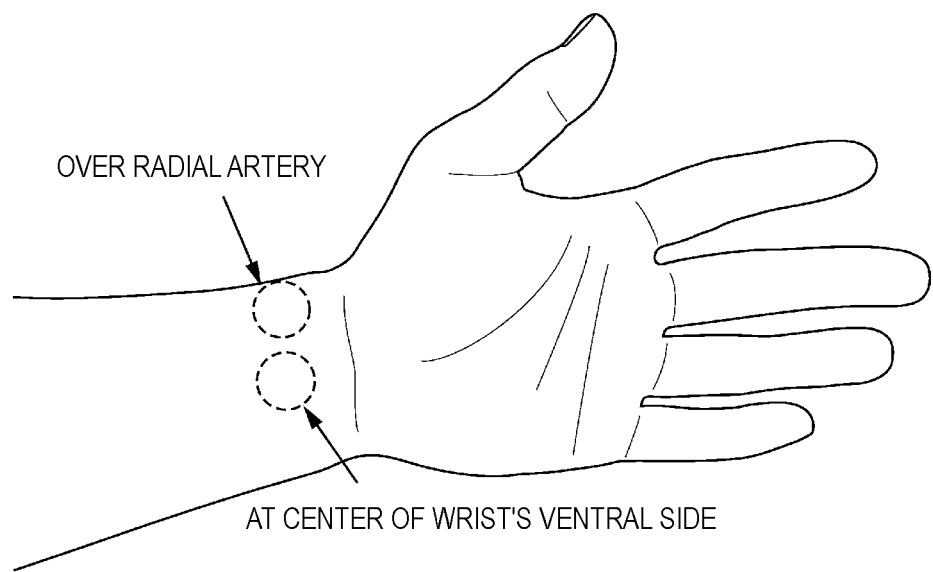
FIG. 4 illustrates the sites of photoplethysmogram measurement in the radial artery.

As a result of the above-mentioned configuration, the first photoplethysmographic sensor 10 is disposed (adjusted) such that when the biological state estimating apparatus 3 is attached to the body, the first photoplethysmographic sensor 10 comes into contact with an area of the epidermis over the radial artery illustrated in FIG. 4. Then, the first photoplethysmographic sensor 10 detects the first photoplethysmographic signal corresponding to the flow of blood in the radial artery. Meanwhile, the second photoplethysmographic sensor 20 detects a photoplethysmographic signal corresponding to the flow of blood in the capillaries at the wrist.

More specifically, the photoplethysmographic signal detected by the second photoplethysmographic sensor 20 with a small optical path length contains hardly any information about the radial artery, which is thick, but contains a large amount of information about the capillaries. By contrast, the photoplethysmographic signal detected by the first photoplethysmographic sensor 10 with a large optical path length contains both information about the thick radial artery and information about the capillaries. In this case, the magnitude of the signal obtained from the thick radial artery is generally greater than that of the signal obtained from the capillaries. Thus, for large optical path lengths, information about the thick radial artery becomes more dominant. A pulse wave sent out from the heart passes through the aorta, branches out to reach the radial artery, and then further branches out to reach the capillaries. Thus, the pulse wave reaches each of these areas with a time difference. Accordingly, by measuring photoplethysmograms in the radial artery and in the capillaries around the radial artery, it is possible to measure pulse transmission time at substantially the same site.

As described above, the first photoplethysmographic sensor 10 and the second photoplethysmographic sensor 20 are each connected to the signal processor 30, and the first photoplethysmographic signal and the second photoplethysmographic signal detected by these sensors are input to the signal processor 30. Hereinafter, the first photoplethysmographic signal and the second photoplethysmographic signal will be sometimes collectively referred to simply as photoplethysmographic signal.

The signal processor 30 also processes the input first and second photoplethysmographic signals to measure pulse rate, pulse interval, and other values. Further, the signal processor 30 measures pulse transmission time from the time difference between the respective peaks of the first and second photoplethysmographic signals detected. At that time, the signal processor 30 corrects a shift (delay) of the peak in each of a first signal processor 310 and a second signal processor 320 described later, and thus measures pulse transmission time with high accuracy.

Then, the signal processor 30 estimates the user's autonomic function based on the measured pulse transmission time, and correlation information that defines the relationship between pulse transmission time and biological state.

The signal processor 30 also determines a pulse rhythm abnormality based on the variability of rate of change in pulse interval acquired. Further, the signal processor 30 determines, based on the measured pulse transmission time, whether the user's body is in a state suitable for sleep, and if it is determined that the user's body is not in a state suitable for sleep, causes the user's body to be put in a state suitable for sleep.

To this end, the signal processor 30 includes components such as amplifiers 311 and 321, the first signal processor 310, the second signal processor 320, peak detectors 316 and 326, peak correctors 318 and 328, a pulse transmission time calculator 330, a pulse transmission time storage 340, a correlation information storage 341, and a biological state estimator 350. The first signal processor 310 includes an analog filter 312, an A/D converter 313, a digital filter 314, and a second-order differentiator 315. The second signal processor 320 includes an analog filter 322, an A/D converter 323, a digital filter 324, and a second-order differentiator 325.

Of the various components mentioned above, the digital filters 314 and 324, the second-order differentiators 315 and 325, the peak detectors 316 and 326, the peak correctors 318 and 328, the pulse transmission time calculator 330, the pulse transmission time storage 340, the correlation information storage 341, and the biological state estimator 350 are implemented by, for example, a CPU that performs arithmetic processing, a ROM that stores a program and data for causing the CPU to execute various processes, and a RAM that temporarily stores various data such as computational results. That is, the functions of the various components mentioned above are preferably implemented by execution of a program stored in the ROM by the CPU.

The amplifier 311 is implemented by, for example, an amplifier such as an operational amplifier. The amplifier 321 amplifies the first photoplethysmographic signal detected by the first photoplethysmographic sensor 10. The first photoplethysmographic signal amplified by the amplifier 311 is output to the first signal processor 310. Likewise, the amplifier 321 is implemented by, for example, an amplifier such as an operational amplifier. The amplifier 321 amplifies the second photoplethysmographic signal detected by the second photoplethysmographic sensor 20. The second photoplethysmographic signal amplified by the amplifier 321 is output to the second signal processor 320.

As described above, the first signal processor 310 includes the analog filter 312, the A/D converter 313, the digital filter 314, and the second-order differentiator 315. The first signal processor 310 applies filtering and second-order differentiation to the first photoplethysmographic signal amplified by the amplifier 311 to extract pulsatile components.

As described above, the second signal processor 320 includes the analog filter 322, the A/D converter 323, the digital filter 324, and the second-order differentiator 325. The second signal processor 320 applies filtering and second-order differentiation to the second photoplethysmographic signal amplified by the amplifier 321 to extract pulsatile components.

The analog filter 312 or 322 and the digital filter 314 or 324 perform a filtering process aimed at improving S/N by removing those components (noise) other than frequencies that characterize a photoplethysmographic signal. The above filtering process is described in more detail below. Generally, the dominant frequency components of a photoplethysmographic signal are those in the vicinity of about 0.1 Hz to several tens of Hz, for example. Accordingly, for improved S/N, filtering is applied by using an analog filter and a digital filter such as a low pass filter and a band pass filter to selectively pass only those portions of the signal in the above frequency range.

If the filtering is only aimed at extraction of pulsatile components, the passband of frequencies may be narrowed to cut off components other than pulsatile components to improve noise resistance. Both of the analog filter 312 or 322 and the digital filter 314 or 324 may not necessarily be provided. Only one of the analog filter 312 or 322 and the digital filter 314 or 324 may be provided. The first photoplethysmographic signal that has undergone filtering with the analog filter 312 and the digital filter 314 is output to the second-order differentiator 315. Likewise, the photoplethysmographic signal that has undergone filtering with the analog filter 322 and the digital filter 324 is output to the second-order differentiator 325.

The second-order differentiator 315 performs second-order differentiation of the first photoplethysmographic signal to acquire a first second-derivative plethysmographic (acceleration plethysmographic) signal. The acquired first acceleration plethysmographic signal is output to the peak detector 316. Peaks on a photoplethysmogram are often not clearly defined and hence difficult to identify. Although this makes it desirable to convert a photoplethysmogram into an acceleration plethysmogram for peak detection, the second-order differentiator 315 may not necessarily be provided.

Likewise, the second-order differentiator 325 performs second-order differentiation of the second photoplethysmographic signal to acquire a second second-derivative plethysmographic (acceleration plethysmographic) signal. The acquired second acceleration plethysmographic signal is output to the peak detector 326. The second-order differentiator 325 may not necessarily be provided.

The peak detector 316 detects a peak of the first photoplethysmographic signal (acceleration plethysmogram) to which filtering has been applied by the first signal processor 310. The peak detector 316 determines that an error condition exists if the amplitude of the first photoplethysmographic signal (or acceleration plethysmogram) is equal to or less than a predetermined value. If it is determined that an error condition exist, it is preferred to move (adjust) the location of the pulse wave sensor 100 (the first photoplethysmographic sensor 10) such that the error condition is eliminated.

The peak detector 326 detects a peak of the second photoplethysmographic signal (acceleration plethysmogram) to which signal processing has been applied by the second signal processor 320. That is, the peak detectors 316 and 326 function as peak detector described in the claims. Each of the peak detector 316 and the peak detector 326 stores, for all of the peaks detected, information such as peak time and peak amplitude in the RAM or other memory areas.

The peak corrector 318 calculates the time delay of the first photoplethysmographic signal in the first signal processor 310 (the analog filter 312, the digital filter 314, and the second-order differentiator 315). The peak corrector 318 corrects the peak of the first photoplethysmographic signal (acceleration plethysmographic signal) detected by the peak detector 316, based on the calculated time delay of the first photoplethysmographic signal. Likewise, the peak corrector 328 calculates the time delay of the second photoplethysmographic signal in the second signal processor 320 (the analog filter 322, the digital filter 324, and the second-order differentiator 325). The peak corrector 328 corrects the peak of the second photoplethysmographic signal (acceleration plethysmographic signal) detected by the peak detector 326, based on the calculated time delay of the second photoplethysmographic signal. The corrected peak of the first photoplethysmographic signal (acceleration plethysmogram), and the corrected peak of the second photoplethysmographic signal (acceleration plethysmogram) are output to the pulse transmission time calculator 330. If the time delay of the first photoplethysmographic signal (acceleration plethysmographic signal) and the time delay of the second photoplethysmographic signal (acceleration plethysmographic signal) can be regarded as substantially equal, the peak correctors 318 and 328 may not necessarily be provided.

The pulse transmission time calculator 330 calculates pulse transmission time from the interval (time difference) between the peak of the first photoplethysmographic signal (acceleration plethysmogram) corrected by the peak corrector 318, and the peak of the second photoplethysmographic signal (acceleration plethysmogram) corrected by the peak corrector 328. That is, the pulse transmission time calculator 330 defines and functions as a pulse transmission time calculator described in the claims.

Figure 5:
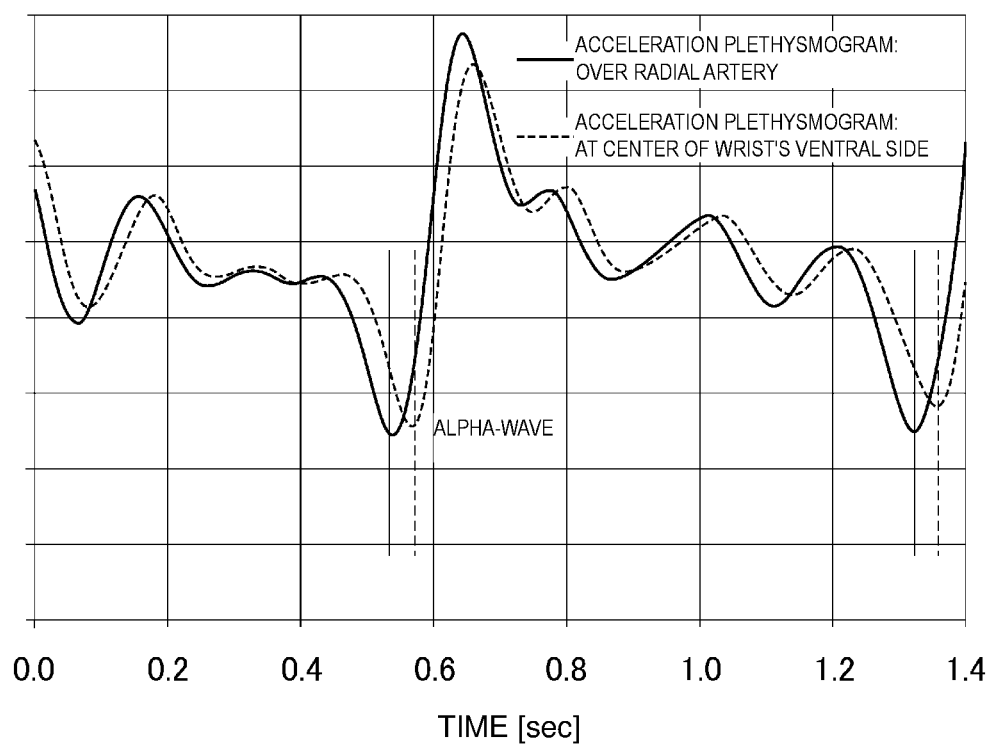
FIG. 5 illustrates an example of photoplethysmograms (acceleration plethysmograms) measured in the radial artery and in the capillaries.

FIG. 5 illustrates pulse transmission time calculated from the interval between a peak of the first photoplethysmographic signal (acceleration plethysmographic signal) and a peak of the second photoplethysmographic signal (acceleration plethysmographic signal). In FIG. 5, the waveform of the first photoplethysmographic signal (acceleration plethysmographic signal) is indicated by a solid line, and the waveform of the second photoplethysmographic signal (acceleration plethysmographic signal) is indicated by a dashed line. As illustrated in FIG. 5, the time difference between the alpha-wave peaks of acceleration plethysmograms obtained from the photoplethysmographic signals detected at two sites corresponding to the radial artery and the capillaries (at the center of the wrist's ventral side in this example (see FIG. 4)) is on the order of about 0.01 second to about 0.04 second. The pulse transmission time calculator 330 determines the detected photoplethysmographic signal to be noise if the calculated pulse transmission time is equal to or less than a predetermined value (for example, about 0.01 second).

In addition to pulse transmission time, the pulse transmission time calculator 330 also calculates, for example, pulse rate, pulse interval, and the rate of change in pulse interval from the photoplethysmographic signal (acceleration plethysmogram). The calculated pulse transmission time, pulse rate, pulse interval, the photoplethysmogram, the acceleration plethysmogram, and other measurement data are output to the pulse transmission time storage 340, the biological state estimator 350, and the display 50.

The pulse transmission time storage 340, which is implemented by, for example, the backup RAM mentioned above stores measurement data such as pulse transmission time calculated by the pulse transmission time calculator 330, together with information such as the date and time of measurement.

The correlation information storage 341, which is implemented by, for example, the ROM mentioned above, stores correlation information defined in advance based on the relationship between pulse transmission time and biological state. That is, the correlation information storage 341 defines and functions as a correlation information storage described in the claims. More specifically, the correlation information storage 341 stores an autonomic function table (corresponding to autonomic function correlation information) determined in advance based on the relationship between pulse transmission time and autonomic function. At that time, the correlation information storage 341 preferably stores correlation information (autonomic function table) representing the relationship between pulse transmission time and biological information (autonomic function), individually for each age and/or each sex.

Dilation and constriction of blood vessels are regulated by the autonomic nervous system, particularly its sympathetic division. Thus, a correlation exists between pulse transmission time, which is closely related with the dilation and constriction of blood vessels, and autonomic function, which indicates the balance between the sympathetic nervous system and the parasympathetic nervous system. Accordingly, a correlation equation or autonomic function table that defines the relationship between pulse transmission time and autonomic function is created in advance based on the measurements of autonomic function and the measurements of pulse transmission time taken at the same instant of time. The created correlation equation or autonomic function table is then stored in the correlation information storage 341. Alternatively, a correlation equation or autonomic function table may be used that defines the relationship between not only pulse transmission time but also LF/HF, which is calculated by the frequency analysis of pulse interval, and autonomic function.

The biological state estimator 350 estimates the user's biological state based on the pulse transmission time obtained by the pulse transmission time calculator 330 and the correlation information stored in the correlation information storage 341. That is, the biological state estimator 350 functions as a biological state estimator described in the claims.

More specifically, the biological state estimator 350 estimates the autonomic function of the user based on pulse transmission time and the autonomic function table (autonomic function correlation information). As described above, the correlation information storage 341 stores the autonomic function table that defines the relationship between pulse transmission time and autonomic function. Thus, the biological state estimator 350 searches the autonomic function table by using the pulse transmission time to estimate autonomic function.

Further, the biological state estimator 350 acquires the rate of change in pulse interval. Then, the biological state estimator 350 determines a pulse rhythm abnormality based on the variability of rate of change in pulse interval acquired. That is, the biological state estimator 350 functions as a pulse interval change rate acquirer and a pulse rhythm abnormality detector that are described in the claims.

Further, the biological state estimator 350 determines that the body is not in a state suitable for sleep if the pulse transmission time calculated by the pulse transmission time calculator 330 is equal to or less than a predetermined threshold. That is, the biological state estimator 350 defines and functions as a sleep state detector described in the claims. The predetermined threshold is set to decrease with increasing pulse interval. Thus, the biological state estimator 350 determines that the body is not in a state suitable for sleep if the pulse transmission time is equal to or less than a predetermined threshold corresponding to the pulse interval, that is, the combination of pulse interval and pulse transmission time is not within a range suitable for sleep. Alternatively, the biological state estimator 350 may determine that the body is not in a state suitable for sleep if the pulse transmission time is equal to or less than a predetermined threshold, irrespective of the pulse interval.

Pulse transmission time tends to decrease when the sympathetic division of the autonomic nervous system is active (dominant), for example, when one is nervous, when tension builds up in the body, or when blood circulation is poor due to constriction of blood vessels (that is, when the body is not in a state suitable for sleep). Further, correlation is considered to exist between the length of pulse interval and the strength of sleepiness. Therefore, when the pulse transmission time is short and the pulse interval is short, such a state is determined to be not suitable for sleep. Conversely, when the pulse transmission time is long and the pulse interval is long, such a state is determined to be suitable for sleep.

A forearm heater 51 heats the forearm (including a part of the forearm (for example, the wrist); the same applies hereinafter) (or increases heat retention in the forearm) to raise the temperature of the forearm if it is determined by the biological state estimator 350 that the user's body is not in a state suitable for sleep. That is, the forearm heater 51 defines and functions as a forearm heater described in the claims.

More specifically, the forearm heater 51 is built in the back side or the belt 210 of the biological state estimating apparatus 3 attached at the wrist. Further, the forearm heater 51 may not be of a wristwatch type but may be in the form of, for example, a wrist band, bracelet, shirt, or sleepwear that includes a heating function. Further, in an alternative possible implementation, the forearm heating function is separated from the biological state estimating apparatus 3, and a component such as a wrist band having such a heating function is controlled based on the determination result supplied from the biological state estimating apparatus 3. The forearm heater 51 heats the forearm (or increases heat retention in the forearm) if it is determined that the user's body is not in a state suitable for sleep. The forearm heater 51 adjusts the output at this time such that the temperature of the forearm increases as the deviation between the pulse transmission time and the above-mentioned predetermined threshold increases. If it is determined that the user's body is in a state suitable for sleep, the forearm heater 51 maintains the state at that time, or decreases the intensity of heating.

Heating may be provided by the forearm heater 51 by, for example, using an electric heater, or tightening the sleeve's edge made of a material with high heat retaining property to provide increased heat retention. The tightening of the sleeve's edge may be varied by, for example, changes in cuff pressure generated by an air pump, or by use of some mechanism. To avoid user discomfort, this heating is preferably performed with a limit placed on the extent of temperature adjustment or with a temperature sensor provided to apply feedback.

Instead of or in addition to the forearm heater 51 mentioned above, the following or similar components may be used in combination as appropriate: a leg heater that, if it is determined that the user's body is not in a state suitable for sleep, heats the leg (including a part of the leg (for example, the ankle)) to raise the temperature of the leg, and a neck cooler that, if it is determined that the user's body is not in a state suitable for sleep, cools the neck to lower the temperature of the neck.

The estimated biological state (that is, autonomic function, pulse rhythm abnormality, and sleep state), and measurement data such as the calculated pulse transmission time, pulse rate, pulse interval, photoplethysmogram, and acceleration plethysmogram are output to a component such as the display 50. Alternatively, the acquired biological state, and measurement data such as pulse transmission time and pulse rate may be accumulated and stored in, for example, the RAM mentioned above in advance so that after the measurement, these pieces of data are output to a smart phone, a personal computer (PC), or other devices and checked.

The display 50 is implemented by, for example, a liquid crystal display (LCD) or an LED. The display 50 displays the following pieces of information in real time: the acquired pulse transmission time, the estimated biological state, measurement data (measurement results) such as pulse rate, and status such as attachment error. The above-mentioned information may be transmitted by a communication section 370 to, for example, a PC, a portable music player having a display, or a smart phone for display on such a device. In that case, preferably, data such as the date and time of measurement is also transmitted in addition to the results of measurement and estimation.

Figure 6:
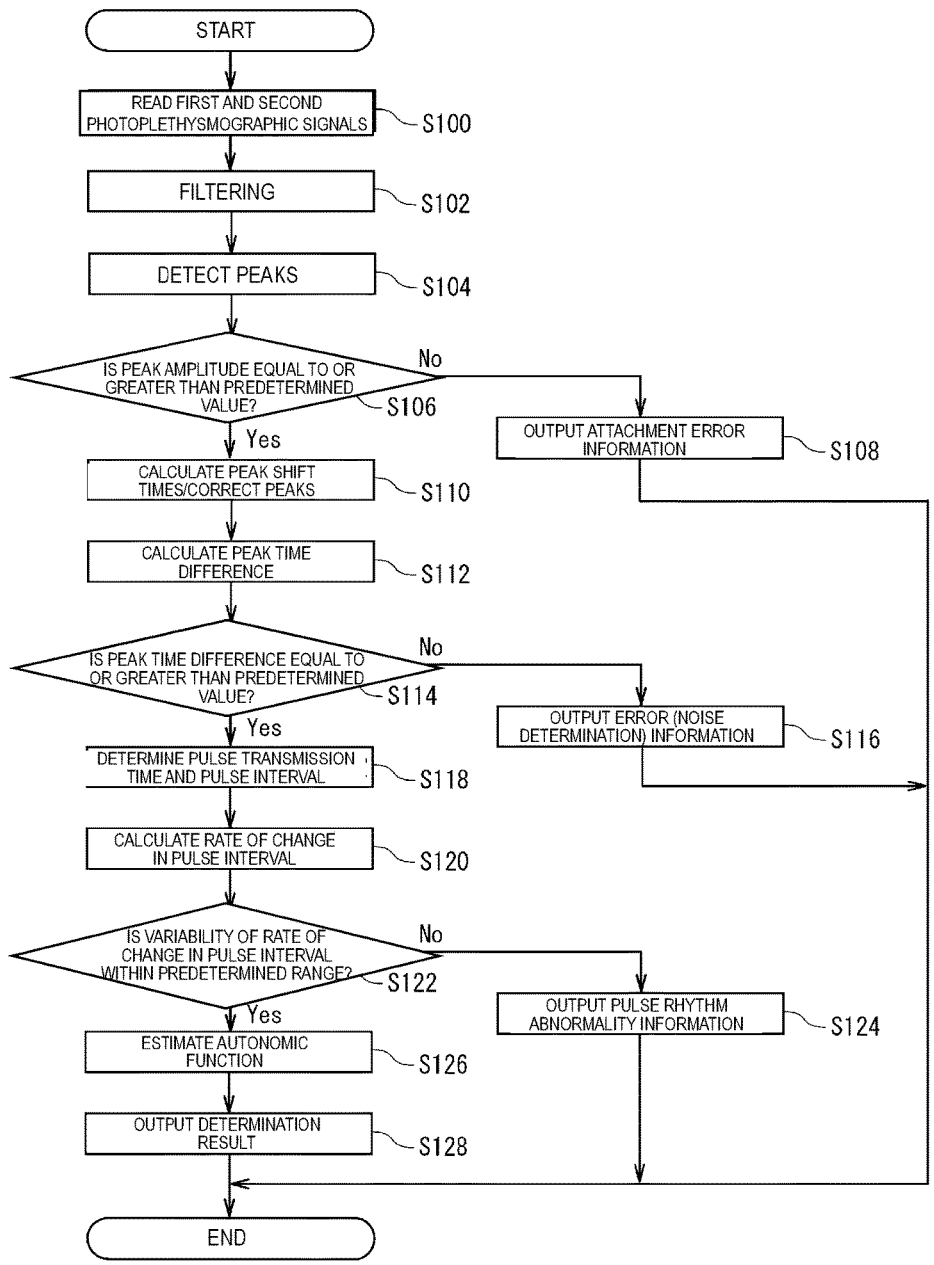
FIG. 6 is a flowchart illustrating the procedure of a biological state (autonomic function) estimation process executed by the biological state estimating apparatus according to a preferred embodiment of the present invention.
Figure 7:
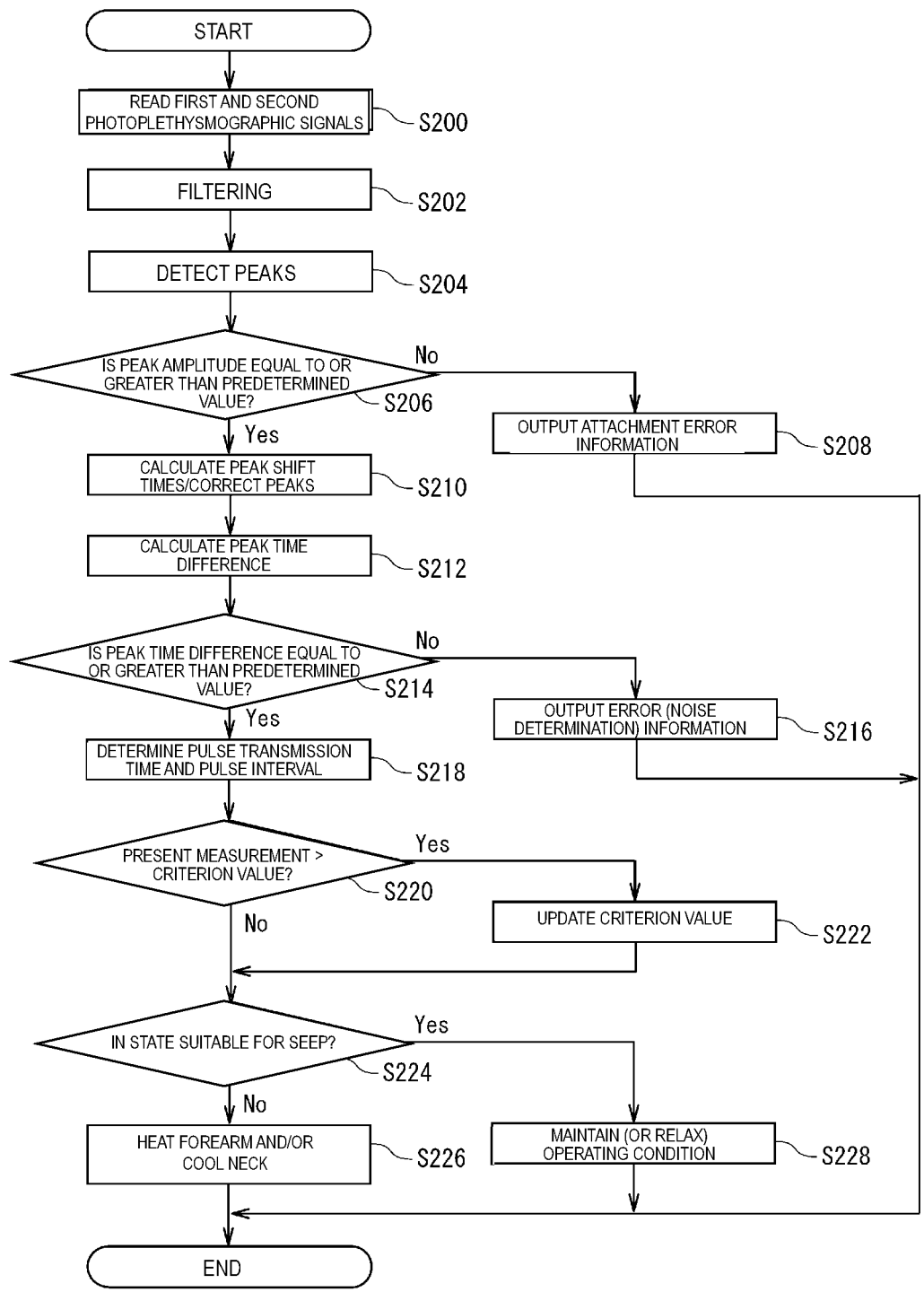
FIG. 7 is a flowchart illustrating the procedure of a sleep support process executed by the biological state estimating apparatus according to a preferred embodiment of the present invention.

Next, operation of the biological state estimating apparatus 3 will be described with reference to FIGS. 6 and 7. FIG. 6 is a flowchart illustrating the procedure of a biological state (autonomic function) estimation process executed by the biological state estimating apparatus 3. FIG. 7 is a flowchart illustrating the procedure of a sleep support process executed by the biological state estimating apparatus 3. The processes illustrated in FIGS. 6 and 7 are mainly executed by the signal processor 30 repeatedly at predetermined time intervals. First, the biological state (autonomic function) estimation process executed by the biological state estimating apparatus 3 will be described with reference to FIG. 6.

At step S100, the first photoplethysmographic signal detected by the first photoplethysmographic sensor 10 and the second photoplethysmographic signal detected by the second photoplethysmographic sensor 20 are read. Subsequently, at step S102, filtering is applied to the first photoplethysmographic signal and the second photoplethysmographic signal read at step S100. Further, second-order differentiation is applied to the first photoplethysmographic signal and the second photoplethysmographic signal to respectively acquire the first acceleration plethysmogram and the second acceleration plethysmogram.

Next, at step S104, the respective peaks of the first photoplethysmographic signal (first acceleration plethysmographic signal) and the second photoplethysmographic signal (second acceleration plethysmographic signal) are detected. Then, peak time, peak amplitude, and other such information are stored for all of the detected peaks.

Subsequently, at step S106, it is determined whether the peak of the first photoplethysmographic signal (first acceleration plethysmographic signal) detected at step S104 has an amplitude equal to or greater than a predetermined value. If the peak of the first photoplethysmographic signal (first acceleration plethysmographic signal) has an amplitude equal to or greater than a predetermined value, the processing transfers to step S110. If the peak of the first photoplethysmographic signal (first acceleration plethysmographic signal) has an amplitude less than a predetermined value, attachment error information (warning information) is output at step S108. Thereafter, the processing temporarily exits from this procedure.

Subsequently, at step S110, the time delay (shift) of the peak of the first photoplethysmographic signal (first acceleration plethysmogram) and the time delay (shift) of the peak of the second photoplethysmographic signal (second acceleration plethysmogram) are determined. Then, the respective peaks of the first photoplethysmographic signal (first acceleration plethysmogram) and the second photoplethysmographic signal (second acceleration plethysmogram) are each corrected based on the determined time delay. Since the method of correcting the peaks is the same as described above, a detailed description in this regard is not provided herein.

Then, at step S112, the time difference (peak time difference) between the corrected peak of the first photoplethysmographic signal (first acceleration plethysmogram), and the corrected peak of the second photoplethysmographic signal (second acceleration plethysmogram) is calculated.

Then, at step S114, it is determined whether the peak time difference calculated at step S112 is equal to or greater than a predetermined value (for example, about 0.01 second). If the peak time difference is equal to or greater than a predetermined value, the processing transfers to step S118. If the peak time difference is less than a predetermined value, error information (noise determination) is output at step S116. Thereafter, the processing temporarily exits from this procedure.

At step S118, the peak time difference calculated at step S112 is determined as the pulse transmission time, and the pulse interval is acquired.

Next, at step S120, the rate of change in the pulse interval acquired at step S118 is calculated, and the variability of rate of change in pulse interval is calculated. Then, at step S122, it is determined whether the variability of rate of change in pulse interval calculated in step S120 is within a predetermined range. If the variability of rate of change in pulse interval is within a predetermined range, the processing transfers to step S126. If the variability of rate of change in pulse interval is not within a predetermined range, pulse rhythm abnormality information is output at step S124. Further, the pulse interval and the pulse transmission time are output at the same time.

At step S126, the autonomic function table is searched by using the pulse transmission time determined at step S118, and autonomic function is estimated. Since the autonomic function table and other details are the same as described above, a detailed description in this regard is not provided herein.

Then, at step S128, the autonomic function estimated at step S126 is output. The pulse transmission time, the pulse interval, and other information are also output at the same time. Thereafter, the processing temporarily exits from this procedure.

Next, the sleep support process executed by the biological state estimating apparatus 3 will be described with reference to FIG. 7.

At step S200, the first photoplethysmographic signal detected by the first photoplethysmographic sensor 10 and the second photoplethysmographic signal detected by the second photoplethysmographic sensor 20 are read. Subsequently, at step S202, filtering is applied to the first photoplethysmographic signal and the second photoplethysmographic signal read at step S200. Further, second-order differentiation is applied to the first photoplethysmographic signal and the second photoplethysmographic signal to respectively acquire the first acceleration plethysmogram and the second acceleration plethysmogram.

Next, at step S204, the respective peaks of the first photoplethysmographic signal (first acceleration plethysmographic signal) and the second photoplethysmographic signal (second acceleration plethysmographic signal) are detected. Then, peak time, peak amplitude, and other such information are stored for all of the detected peaks.

Subsequently, at step S206, it is determined whether the peak of the first photoplethysmographic signal (first acceleration plethysmographic signal) detected at step S204 has an amplitude equal to or greater than a predetermined value.

If the peak of the first photoplethysmographic signal (first acceleration plethysmographic signal) has an amplitude equal to or greater than a predetermined value, the processing transfers to step S210. If the peak of the first photoplethysmographic signal (first acceleration plethysmographic signal) has an amplitude less than a predetermined value, attachment error information (warning information) is output at step S208. Thereafter, the processing temporarily exits from this procedure.

At step S210, the time delay (shift) of the peak of the first photoplethysmographic signal (first acceleration plethysmogram) and the time delay (shift) of the peak of the second photoplethysmographic signal (second acceleration plethysmogram) are calculated. Then, the respective peaks of the first photoplethysmographic signal (first acceleration plethysmogram) and the second photoplethysmographic signal (second acceleration plethysmogram) are each corrected based on the determined time delay. Since the method of correcting the peaks is the same as described above, a detailed description in this regard is not provided herein.

Then, at step S212, the time difference (peak time difference) between the corrected peak of the first photoplethysmographic signal (first acceleration plethysmogram), and the corrected peak of the second photoplethysmographic signal (second acceleration plethysmogram) is calculated.

Then, at step S214, it is determined whether the peak time difference calculated at step S212 is equal to or greater than a predetermined time (for example, about 0.01 second). If the peak time difference is equal to or greater than a predetermined value, the processing transfers to step S218. If the peak time difference is less than a predetermined value, error information (noise determination) is output at step S216. Thereafter, the processing temporarily exits from this procedure.

At step S218, the peak time difference calculated at step S212 is determined as the pulse transmission time, and the pulse interval is acquired.

Next, at step S220, it is determined whether the pulse transmission time calculated at step S218 (the present measurement) is greater than the criterion value (the maximum value of pulse transmission time) currently stored. If the pulse transmission time (the present measurement) is greater than the criterion value currently stored, the processing transfers to step S222. If the pulse transmission time (the present measurement) is equal to or less than the criterion value currently stored, the processing transfers to step S224.

At step S222, the criterion value (the maximum value of pulse transmission time) is updated. That is, the pulse transmission time obtained at step S218 (the present measurement) is stored as a new criterion value. Further, a predetermined threshold to determine whether the user's body is in a state suitable for sleep is reset based on the new criterion value. Then, the processing transfers to step S224.

At step S224, it is determined whether the pulse transmission time is greater than a predetermined threshold corresponding to the pulse interval, that is, whether the user's body is in a state suitable for sleep. If the pulse transmission time is greater than a predetermined threshold corresponding to the pulse interval, that is, if the user's body is in a state suitable for sleep, the processing transfer to step S228. If the pulse transmission time is equal to or less than a predetermined threshold corresponding to the pulse interval, that is, if the user's body is not in a state suitable for sleep, the processing transfers to step S226.

At step S226, the temperature of the forearm is raised by heating the forearm (for example, the wrist) (or increasing heat retention in the forearm). Alternatively, the temperature of the neck is lowered by cooling the neck. This puts the user's body in a state suitable for sleep. Thereafter, the processing temporarily exits from this procedure.

At step S228, the operating condition of a component such as the forearm heater 51 is maintained without being changed (or the operating condition is relaxed), and the user's body is maintained in a state suitable for sleep. Thereafter, the processing temporarily exits from this procedure.

As described above, in the present preferred embodiment, the first photoplethysmographic sensor 10 and the second photoplethysmographic sensor 20 are disposed on the contact surface 1a that comes into contact with the body when the biological state estimating apparatus 3 is attached to the body. Thus, by simply attaching the biological state estimating apparatus 3 to the user such that the contact surface 1a comes into contact with the body, the second photoplethysmographic signal corresponding to the flow of blood in the capillaries, and the first photoplethysmographic signal corresponding to the flow of blood in an artery thicker than the capillaries are able to be detected. This configuration allows for easier attachment to the body, and enables continuous measurement of pulse transmission time during activities (during daily life).

According to the present preferred embodiment, the spacing between the second light emitter 21 and the second light receiver 22 is preferably shorter than the spacing between the first light emitter 11 and the first light receiver 12. This configuration allows the second photoplethysmographic sensor 20 to detect the second photoplethysmographic signal corresponding to the flow of blood in the capillaries located close to the epidermis (that is, at a shallow depth). By contrast, the first photoplethysmographic sensor 10 is able to detect the first photoplethysmographic signal corresponding to the flow of blood in an artery located distant from the epidermis (that is, at a deep depth) and thicker than the capillaries.

The blue to yellow-green wave lengths of light in the range of about 450 nm to about 580 nm are subject to strong absorption in living bodies. Thus, these wave lengths of light allow for greater output of the resulting photoplethysmographic signal but do not allow the optical path length to be extended. By contrast, near-infrared light with wave lengths in the range of about 800 nm to about 1000 nm is not subject to strong absorption in living bodies. Thus, such near-infrared light provides smaller output of the resulting photoplethysmographic signal but allows for extended optical path length. Therefore, the present preferred embodiment allows for improved S/N compared to when sources of light of the same wave length are used as the first light emitter 11 and the second light emitter 21.

Detection of a photoplethysmographic signal at an artery located distant from the epidermis (that is, at a deep depth) and thicker than the capillaries is subject to high dependency on the detecting location. That is, displacement of the detecting location from that suitable for detection may make it impossible to properly detect a photoplethysmographic signal. According to the present preferred embodiment, if the amplitude of the first photoplethysmographic signal is equal to or less than a predetermined value, this is determined to be an error, thus allowing displacement of the detecting location to be recognized. This makes it possible to prevent measurements from being taken with such displacement of the detecting location left as it is.

According to the present preferred embodiment, the pulse wave sensor 100 (the first photoplethysmographic sensor 10) is configured to be movable. Thus, if, for example, attachment error information is output, the location of the pulse wave sensor 100 (the first photoplethysmographic sensor 10) is able to be adjusted without detaching the apparatus from the user's body.

According to the present preferred embodiment, the first photoplethysmographic sensor 10 and the second photoplethysmographic sensor 20 are disposed on the contact surface 1a that comes into contact with the wrist when the biological state estimating apparatus 3 is attached to the body, and the first photoplethysmographic sensor 10 detects the first photoplethysmographic signal corresponding to the flow of blood in the radial artery. Among various arteries, which are thick, the radial artery in particular is located at a relatively shallow depth from the epidermis. Thus, the configuration according to the present preferred embodiment allows for stable measurement of the first photoplethysmographic signal. Furthermore, the apparatus is attached at the wrist, thus creating relatively less user resistance to attachment of the apparatus. This allows the apparatus to be attached on the user's body for an extended period of time without giving a sense of discomfort.

According to the present preferred embodiment, the pulse wave sensor 100 (the first photoplethysmographic sensor 10) is disposed on the contact surface 1a such that when the biological state estimating apparatus 3 is attached to the body, the pulse wave sensor 100 comes into contact with an area of the epidermis over the radial artery. This configuration allows for easy positioning of the pulse wave sensor 100 (the first photoplethysmographic sensor 10) even when the user is unable to accurately identify where the radial artery is located.

The radial artery is located deeper from the epidermis than the capillaries. According to the present preferred embodiment, the area of the contact surface 1a where the first photoplethysmographic sensor 10 is disposed protrudes in a smooth convex shape toward the wrist. This configuration allows the first photoplethysmographic sensor 10 to be pressed toward the wrist to ensure more stable measurement of the first photoplethysmographic signal.

According to the present preferred embodiment, if the pulse transmission time obtained is equal to or less than a predetermined value, this is determined as noise. This makes it possible to easily and properly discriminate noise superimposed on the pulse wave signal, for example, noise resulting from body movements.

According to the present preferred embodiment, a pulse rhythm abnormality due to arrhythmia is able to be easily and properly determined. In this case, in particular, the biological state estimating apparatus 3 includes the pulse transmission time measuring apparatus 1 configured as mentioned above. This allows for easier attachment to the body, and also enables continuous detection of a pulse rhythm abnormality during activities (during daily life).

According to the present preferred embodiment, if the pulse transmission time is equal to or less than a predetermined threshold, it is determined that the user's body is not in a state suitable for sleep. It is thus possible to determine whether the user's body is in a state suitable for sleep. In particular, in this case, the biological state estimating apparatus 3 includes the pulse transmission time measuring apparatus 1 configured as mentioned above, thus allowing for easier attachment to the body.

According to the present preferred embodiment, if the user's body is not in a state suitable for sleep, the temperature of the user's forearm is raised. This allows only the forearm to be heated without raising the temperature of the trunk of the body. This puts the user's body in a state in which the forearm is heated to cause the peripheral blood vessels in the fingers to widen, with the temperature of the trunk of the body remaining low, in other words, a state suitable for sleep. It is thus possible for the user to smoothly get to sleep (fall asleep) and obtain deep sleep.

Further, according to the present preferred embodiment, the autonomic function table (autonomic function correlation information) defined in advance based on the relationship between pulse transmission time and autonomic function is stored. Thus, by measuring the pulse transmission time of the user, and using the measured pulse transmission time as an index, autonomic function as an example of biological state is able to be estimated for evaluation. In particular, the time difference between the respective peaks of pulse waves obtained from the thick artery and the capillaries is measured. This allows the influence of the capillaries to be strongly reflected, thus enabling estimation of autonomic activities, coldness of the hand/blood circulation, and other conditions related to the constriction/dilation of blood vessels. Further, in this case, the biological state estimating apparatus 3 includes the pulse transmission time measuring apparatus 1 configured as mentioned above. This allows for easier attachment to the body, and also enables continuous estimation and evaluation of autonomic function during activities (during daily life).

First Modification

Figure 8:
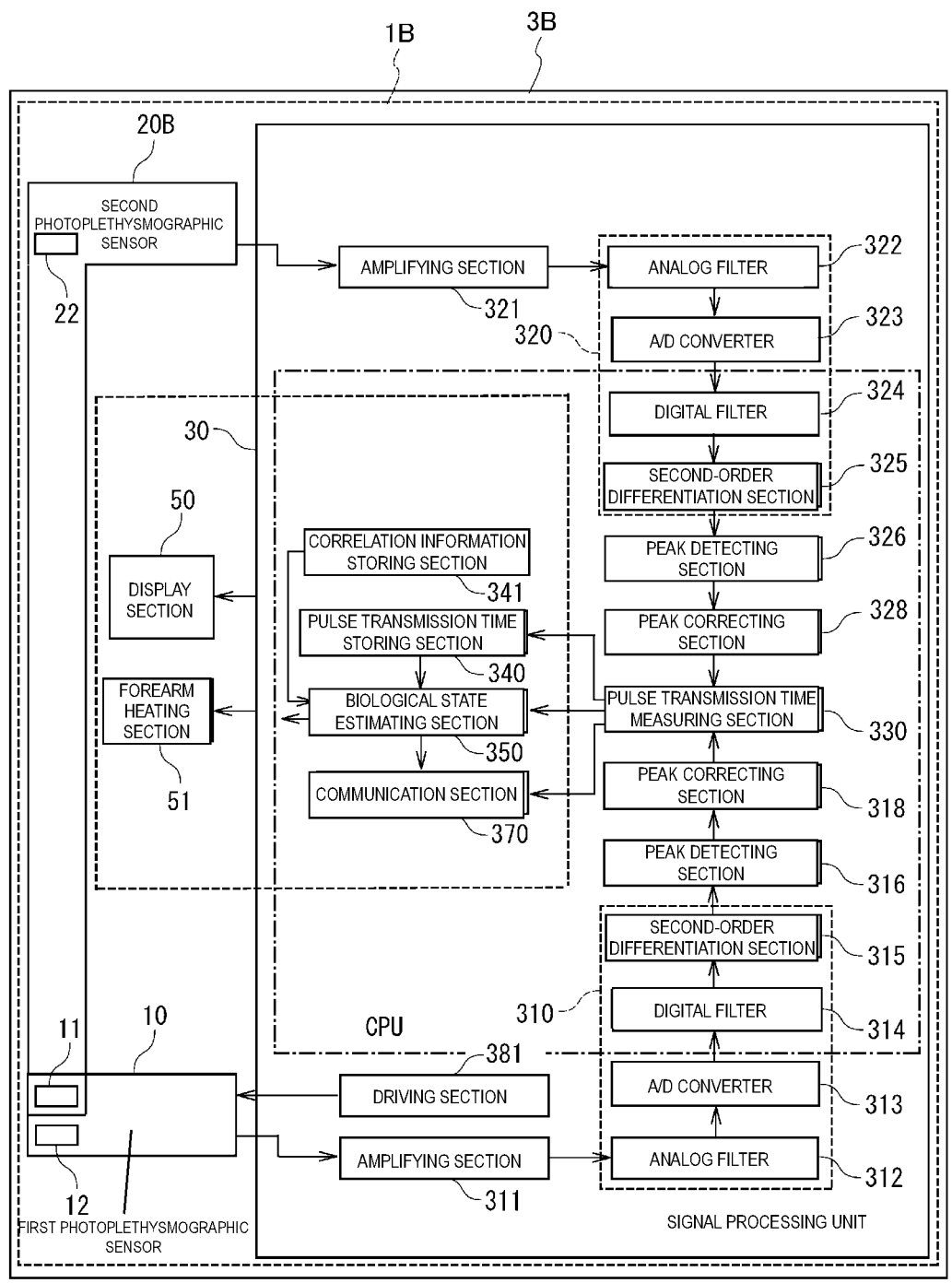
FIG. 8 is a block diagram illustrating the configuration of a biological state estimating apparatus including a pulse transmission time measuring apparatus according to a first modification of a preferred embodiment of the present invention.

In the preferred embodiment of the present invention described above, the first photoplethysmographic sensor 10 including the first light emitter 11 and the first light receiver 12, and the second photoplethysmographic sensor 20 including the second light emitter 21 and the second light receiver 22 are used to respectively detect the first and second photoplethysmographic signals. Alternatively, as illustrated in FIG. 8, the first light emitter 11 and the second light emitter 21 may be made common (that is, shared by the first photoplethysmographic sensor 10 and the second photoplethysmographic sensor 20). FIG. 8 is a block diagram illustrating the configuration of a biological state estimating apparatus 3B including a pulse transmission time measuring apparatus 1B according to a first modification of a preferred embodiment of the present invention. In FIG. 8, components identical or equivalent to those in the preferred embodiment mentioned above are denoted by the same reference signs.

In the pulse transmission time measuring apparatus 1B according to the first modification, the first photoplethysmographic sensor 10 includes the first light emitter 11 and the first light receiver 12, and detects the first photoplethysmographic signal as in the preferred embodiments mentioned above. A second photoplethysmographic sensor 20B includes the first light emitter 11 and the second light receiver 22, and detects the second photoplethysmographic signal.

The first photoplethysmographic sensor 10 and the second photoplethysmographic sensor 20B are disposed on the pulse wave sensor 100. At that time, the spacing between the first light emitter 11 and the second light receiver 22 is set less than the spacing between the first light emitter 11 and the first light receiver 12. The first modification is otherwise identical or similar in configuration to the biological state estimating apparatus 3 (the pulse transmission time measuring apparatus 1) mentioned above, and thus a detailed description in this regard is not provided herein.

Examples of suitable methods to isolate the first photoplethysmographic signal and the second photoplethysmographic signal from each other include those based on time division (causing detected beams of light to be emitted in a pulsed fashion and shifting the timing of their emissions relative to each other), those based on wave length division (disposing a wave filter corresponding to each individual wave length in front of the light receiver), and those based on space division (spacing the detected beams of light apart to avoid their mutual interference).

As with the above-mentioned preferred embodiment, the first modification allows for easier attachment to the body, and enables continuous measurement of pulse transmission time during activities (during daily life). In this case, the sharing of the same light emitter allows for, for example, reduced size, weight, and cost of the apparatus.

According to the first modification, the spacing between the first light emitter 11 and the second light receiver 22 is preferably shorter than the spacing between the first light emitter 11 and the first light receiver 12. This configuration allows the second photoplethysmographic sensor 20B to detect the second photoplethysmographic signal corresponding to the flow of blood in the capillaries located close to the epidermis (that is, at a shallow depth). By contrast, the first photoplethysmographic sensor 10 is able to detect the first photoplethysmographic signal corresponding to the flow of blood in an artery located distant from the epidermis (that is, at a deep depth) and thicker than the capillaries.

Second Modification

Figure 9:
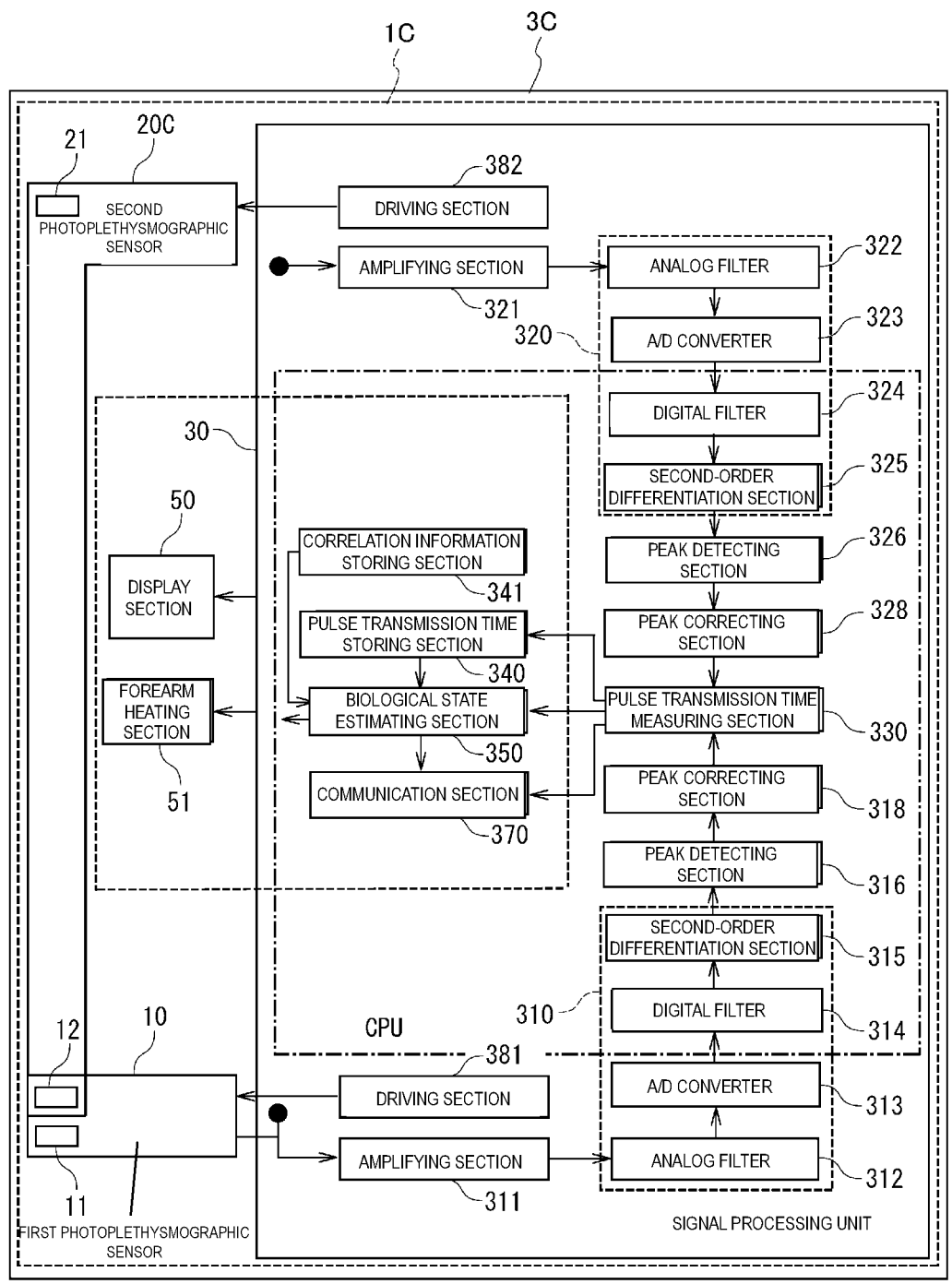
FIG. 9 is a block diagram illustrating the configuration of a biological state estimating apparatus including a pulse transmission time measuring apparatus according to a second modification of a preferred embodiment of the present invention.

In the preferred embodiments of the present invention mentioned above, the first photoplethysmographic sensor 10 including the first light emitter 11 and the first light receiver 12, and the second photoplethysmographic sensor 20 including the second light emitter 21 and the second light receiver 22 are used to respectively detect the first and second photoplethysmographic signals. Alternatively, as illustrated in FIG. 9, the first light receiver 12 and the second light receiver 22 may be made common (that is, shared by the first photoplethysmographic sensor 10 and the second photoplethysmographic sensor 20). FIG. 9 is a block diagram illustrating the configuration of a biological state estimating apparatus 3C including a pulse transmission time measuring apparatus 1C according to a second modification. In FIG. 9, components identical or equivalent to those in the preferred embodiments mentioned above are denoted by the same reference signs. In this case, components such as an amplifier may be shared as well.

In the pulse transmission time measuring apparatus 1C according to the second modification, the first photoplethysmographic sensor 10 includes the first light emitter 11 and the first light receiver 12, and detects the first photoplethysmographic signal as in the preferred embodiment mentioned above. A second photoplethysmographic sensor 20C includes the second light emitter 21 and the first light receiver 12, and detects the second photoplethysmographic signal.

The first photoplethysmographic sensor 10 and the second photoplethysmographic sensor 20C are disposed on the pulse wave sensor 100. At that time, the spacing between the second light emitter 21 and the first light receiver 12 is set less than the spacing between the first light emitter 11 and the first light receiver 12. The second modification is otherwise identical or similar in configuration to the biological information state apparatus 3 (the pulse transmission time measuring apparatus 1) mentioned above, and thus a detailed description in this regard is not provided herein.

Examples of suitable methods to isolate the first photoplethysmographic signal and the second photoplethysmographic signal from each other include those based on time division (causing detected beams of light to be emitted in a pulsed fashion and shifting the timing of their emissions relative to each other), those based on wave length division (disposing a wave filter corresponding to each individual wave length in front of the light receiver), and those based on space division (spacing the detected beams of light apart to avoid their mutual interference).

As with the above-mentioned preferred embodiments, the second modification allows for easier attachment to the body, and enables continuous measurement of pulse transmission time during activities (during daily life). In this case, the sharing of the same light receiver allows for, for example, reduced size, weight, and cost of the apparatus.

According to the second modification, the spacing between the second light emitter 21 and the first light receiver 12 is preferably shorter than the spacing between the first light emitter 11 and the first light receiver 12. This configuration allows the second photoplethysmographic sensor 20C to detect the second photoplethysmographic signal corresponding to the flow of blood in the capillaries located close to the epidermis (that is, at a shallow depth). By contrast, the first photoplethysmographic sensor 10 is able to detect the first photoplethysmographic signal corresponding to the flow of blood in an artery located distant from the epidermis (that is, at a deep depth) and thicker than the capillaries.

Third Modification

Figure 10:
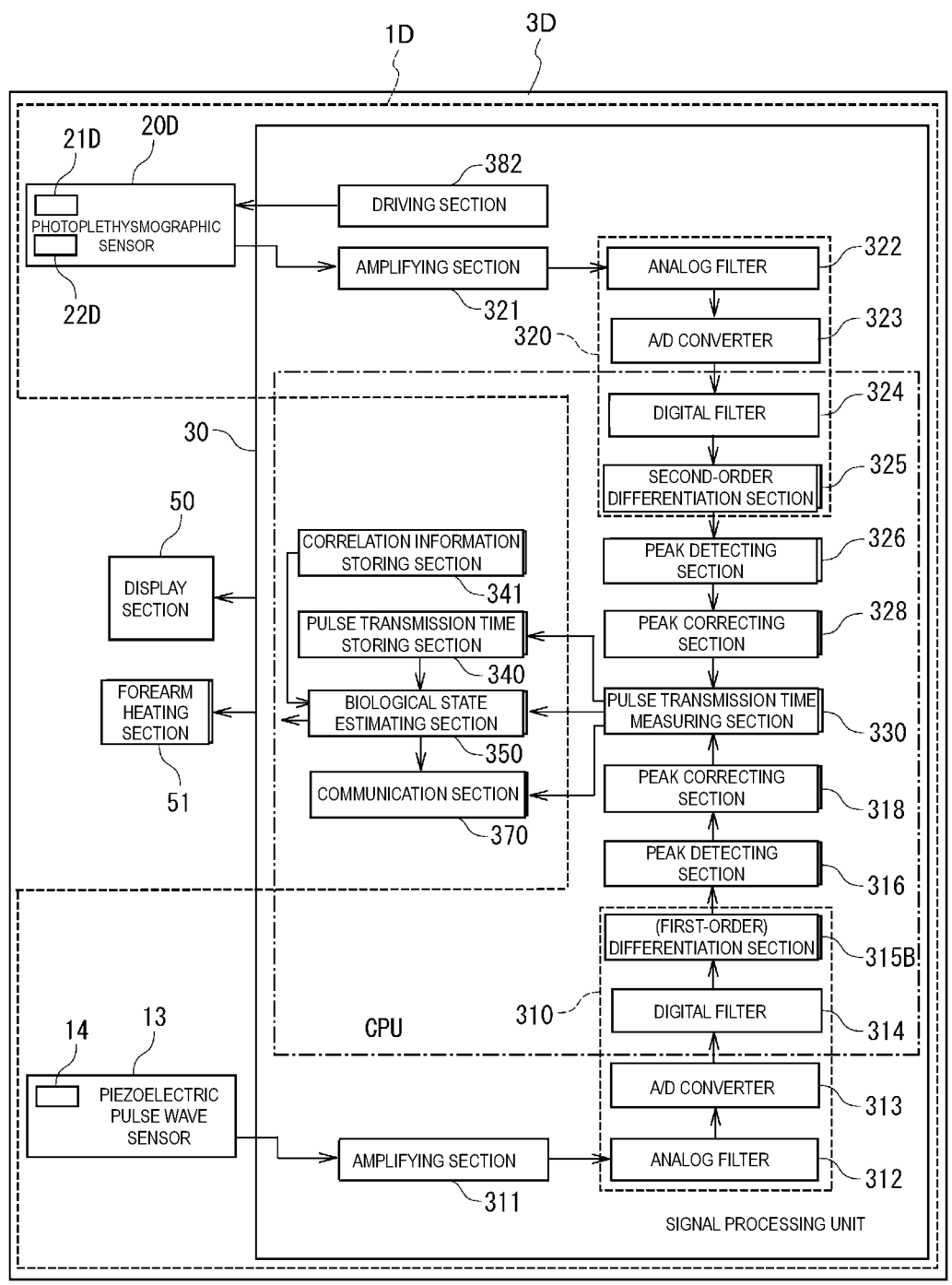
FIG. 10 is a block diagram illustrating the configuration of a biological state estimating apparatus including a pulse transmission time measuring apparatus according to a third modification of a preferred embodiment of the present invention.

In the preferred embodiment mentioned above, the first photoplethysmographic sensor 10 including the first light emitter 11 and the first light receiver 12 is used to detect the first photoplethysmographic signal corresponding to the flow of blood in the radial artery. Alternatively, as illustrated in FIG. 10, a piezoelectric pulse wave sensor 13 that includes a piezoelectric element 14 and detects a piezoelectric pulse wave signal may be used instead of the first photoplethysmographic sensor 10. FIG. 10 is a block diagram illustrating the configuration of a biological state estimating apparatus 3D including a pulse transmission time measuring apparatus 1D according to a third modification of a preferred embodiment of the present invention. In FIG. 10, components identical or equivalent to those in the preferred embodiments of the present invention described above are denoted by the same reference signs.

In the pulse transmission time measuring apparatus 1D according to the third modification, the piezoelectric pulse wave sensor 13 detects a piezoelectric pulse wave signal corresponding to the flow of blood (pulsation) in the radial artery. A photoplethysmographic sensor 20D includes a light emitter 21D and a light receiver 22D, and detects a photoplethysmographic signal corresponding to the flow of blood in the capillaries.

The piezoelectric pulse wave sensor 13 is disposed on the pulse wave sensor 100 mentioned above. The third modification is otherwise identical or similar in configuration to the biological state estimating apparatus 3 (the pulse transmission time measuring apparatus 1) mentioned above, and thus a detailed description in this regard is not provided herein. Unlike photoplethysmographic pulse waves, piezoelectric pulse waves are velocity pulse waves. Accordingly, a (first-order) differentiator 315B is used instead of the second-order differentiator 315 mentioned above.

As with the above-mentioned preferred embodiment, the third modification allows for easier attachment to the body, and enables continuous measurement of pulse transmission time during activities (during daily life).

While preferred embodiments of the present invention has been described above, the present invention is not limited to the above-mentioned preferred embodiments but can be practiced with various modifications. For example, although the above-mentioned preferred embodiments are preferably directed to the biological state estimating apparatus 3 of a wristwatch type, the type of the biological state estimating apparatus used is not limited to the wristwatch type. For example, the biological state estimating apparatus 3 may be of a wrist band type, or may be of a type placed at the edge of the sleeve of a garment such as a shirt. For example, in the case of a wrist band-type biological state estimating apparatus, the first photoplethysmographic sensor 10 and the second photoplethysmographic sensor 20 are attached on the inner side of a wrist band made of a stretchable material to ensure that these sensors come into close contact with the user's wrist when the biological state estimating apparatus is attached to the body.

Although the above-mentioned preferred embodiments preferably measures pulse transmission time at the wrist where the radial artery is located, the site to measure pulse transmission time is not limited to the wrist. For example, pulse transmission time may be measured at a site such as the neck where the carotid artery is located, the elbow where the brachial artery is located, or the temple where the superficial temporal artery is located.

Although the above-mentioned preferred embodiments preferably uses the autonomic function table to estimate the biological state (autonomic function) of the user, the biological state may be estimated by calculation based on a correlation equation.

Measurement data such as the pulse signal and pulse transmission time acquired may be output to and displayed on a device such as a PC, a portable music player having a display, or a smart phone. In that case, estimation of the biological state may be performed on the PC or smart phone. Further, data may be transmitted to a server and processed on the server. In this case, data such as the correlation information mentioned above is stored on the PC, smart phone, or server.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A pulse transmission time measuring apparatus comprising:
   a first photoplethysmographic sensor that includes a first light emitter and a first light receiver, and detects a first photoplethysmographic signal;
   a second photoplethysmographic sensor that includes a second light emitter and a second light receiver, and detects a second photoplethysmographic signal;
   a peak detector that detects a peak of the first photoplethysmographic signal detected by the first photoplethysmographic sensor, and a peak of the second photoplethysmographic signal detected by the second photoplethysmographic sensor; and
   a pulse transmission time calculator that calculates a pulse transmission time from a time difference between the peak of the first photoplethysmographic signal detected by the peak detector and the peak of the second photoplethysmographic signal detected by the peak detector; wherein the first photoplethysmographic sensor and the second photoplethysmographic sensor are disposed on a contact surface of the pulse transmission time measuring apparatus that, when the pulse transmission time measuring apparatus is attached to a body, comes into contact with the body;

the second photoplethysmographic sensor detects the second photoplethysmographic signal corresponding to flow of blood in capillaries; and the first photoplethysmographic sensor detects the first photoplethysmographic signal corresponding to flow of blood in an artery thicker than the capillaries.

2. The pulse transmission time measuring apparatus according to claim 1, wherein the second light emitter and the second light receiver are separated by a spacing that is less than a spacing between the first light emitter and the first light receiver.

3. The pulse transmission time measuring apparatus according to claim 1, wherein the first light emitter outputs light with a wave length of about 800 nm to about 1000 nm, and the second light emitter outputs light with a wave length of about 450 nm to about 580 nm.

4. The pulse transmission time measuring apparatus according to claim 1, wherein the peak detector determines that an error condition exists if the first photoplethysmographic signal has an amplitude equal to or less than a predetermined value.

5. The pulse transmission time measuring apparatus according to claim 1, wherein the first photoplethysmographic sensor is capable of being varied in location.

6. The pulse transmission time measuring apparatus according to claim 1, wherein the first photoplethysmographic sensor and the second photoplethysmographic sensor are disposed on a contact surface of the pulse transmission time measuring apparatus that comes into contact with a wrist when the pulse transmission time measuring apparatus is attached to the body; and the first photoplethysmographic sensor detects the first photoplethysmographic signal corresponding to flow of blood in a radial artery.

7. The pulse transmission time measuring apparatus according to claim 6, wherein the first photoplethysmographic sensor is disposed on the contact surface such that when the pulse transmission time measuring apparatus is attached to the body, the first photoplethysmographic sensor comes into contact with an area of an epidermis over the radial artery.

8. The pulse transmission time measuring apparatus according to claim 1, wherein an area of the contact surface where the first photoplethysmographic sensor is disposed has a shape that, when the pulse transmission time measuring apparatus is attached to the body, protrudes in a convex manner toward a wrist relative to an area of the contact surface where the first photoplethysmographic sensor is not disposed.

9. The pulse transmission time measuring apparatus according to claim 1, wherein the pulse transmission time calculator determines that an error condition exists if the pulse transmission time calculated by the pulse transmission time calculator is equal to or less than a predetermined value.

10. A biological state estimating apparatus comprising:
the pulse transmission time measuring apparatus according to claim 1;
a pulse interval change rate acquirer that acquires a rate of change in pulse interval; and
a pulse rhythm abnormality detector that determines a pulse rhythm abnormality based on variability of the rate of change in pulse interval acquired by the pulse interval change rate acquirer.

11. A biological state estimating apparatus comprising:
the pulse transmission time measuring apparatus according to claim 1; and
a sleep state detector that determines that a body is not in a state suitable for sleep if the pulse transmission time calculated by the pulse transmission time calculator is equal to or less than a predetermined threshold.

12. The biological state estimating apparatus according to claim 11, further comprising a forearm heater that, if it is determined by the sleep state detector that the body is not in a state suitable for sleep, raises a temperature of a forearm.

13. A biological state estimating apparatus comprising:
the pulse transmission time measuring apparatus according to claim 1;
a correlation information storage that stores autonomic function correlation information, the autonomic function correlation information being defined in advance based on a relationship between pulse transmission time and autonomic function; and
a biological state estimator that estimates an autonomic function of a user based on the pulse transmission time calculated by the pulse transmission time calculator, and the autonomic function correlation information stored in the correlation information storage.

14. A pulse transmission time measuring apparatus comprising:
a first photoplethysmographic sensor that includes a first light emitter and a first light receiver, and detects a first photoplethysmographic signal;
a second photoplethysmographic sensor that includes the first light emitter and a second light receiver, and detects a second photoplethysmographic signal;
a peak detector that detects a peak of the first photoplethysmographic signal detected by the first photoplethysmographic sensor, and a peak of the second photoplethysmographic signal detected by the second photoplethysmographic sensor; and
a pulse transmission time calculator that calculates a pulse transmission time from a time difference between the peak of the first photoplethysmographic signal detected by the peak detector and the peak of the second photoplethysmographic signal detected by the peak detector; wherein the first photoplethysmographic sensor and the second photoplethysmographic sensor are disposed on a contact surface of the pulse transmission time measuring apparatus that, when the pulse transmission time measuring apparatus is attached to a body, comes into contact with the body;

the second photoplethysmographic sensor detects the second photoplethysmographic signal corresponding to flow of blood in capillaries; and the first photoplethysmographic sensor detects the first photoplethysmographic signal corresponding to flow of blood in an artery thicker than the capillaries.

15. The pulse transmission time measuring apparatus according to claim 14, wherein the first light emitter and the second light receiver are separated by a spacing that is less than a spacing between the first light emitter and the first light receiver.

16. A pulse transmission time measuring apparatus, comprising:
a first photoplethysmographic sensor that includes a first light emitter and a first light receiver, and detects a first photoplethysmographic signal;
a second photoplethysmographic sensor that includes a second light emitter and the first light receiver, and detects a second photoplethysmographic signal;
a peak detector that detects a peak of the first photoplethysmographic signal detected by the first photoplethysmographic sensor, and a peak of the second photoplethysmographic signal detected by the second photoplethysmographic sensor; and
a pulse transmission time calculator that calculates a pulse transmission time from a time difference between the peak of the first photoplethysmographic signal detected by the peak detector and the peak of the second photoplethysmographic signal detected by the peak detector; wherein
the first photoplethysmographic sensor and the second photoplethysmographic sensor are disposed on a contact surface of the pulse transmission time measuring apparatus that, when the pulse transmission time measuring apparatus is attached to a body, comes into contact with the body;
the second photoplethysmographic sensor detects the second photoplethysmographic signal corresponding to flow of blood in capillaries; and
the first photoplethysmographic sensor detects the first photoplethysmographic signal corresponding to flow of blood in an artery thicker than the capillaries.

17. The pulse transmission time measuring apparatus according to claim 16, wherein the second light emitter and the first light receiver are separated by a spacing that is less than a spacing between the first light emitter and the first light receiver.

18. The pulse transmission time measuring apparatus according to claim 16, wherein
the first light emitter outputs light with a wave length of about 800 nm to about 1000 nm; and
the second light emitter outputs light with a wave length of about 450 nm to about 580 nm.

19. A pulse transmission time measuring apparatus comprising:
a photoplethysmographic sensor that includes a light emitter and a light receiver, and detects a photoplethysmographic signal;
a piezoelectric pulse wave sensor that includes a piezoelectric element and detects a piezoelectric pulse wave signal;
a peak detector that detects a peak of the photoplethysmographic signal detected by the photoplethysmographic sensor, and a peak of the piezoelectric pulse wave signal detected by the piezoelectric pulse wave sensor; and
a pulse transmission time calculator that calculates a pulse transmission time from a time difference between the peak of the photoplethysmographic signal detected by the peak detector and the peak of the piezoelectric pulse wave signal detected by the peak detector; wherein
the photoplethysmographic sensor and the piezoelectric pulse wave sensor are disposed on a contact surface of the pulse transmission time measuring apparatus that, when the pulse transmission time measuring apparatus is attached to a body, comes into contact with the body;
the photoplethysmographic sensor detects the photoplethysmographic signal corresponding to flow of blood in capillaries; and
the piezoelectric pulse wave sensor detects the piezoelectric pulse wave signal corresponding to flow of blood in an artery thicker than the capillaries.

20. The pulse transmission time measuring apparatus according to claim 19, wherein the peak detector determines that an error condition exists if the piezoelectric pulse wave signal has an amplitude equal to or less than a predetermined value.

21. The pulse transmission time measuring apparatus according to claim 19, wherein the piezoelectric pulse wave sensor is capable of being varied in location.

22. The pulse transmission time measuring apparatus according to claim 19, wherein
the photoplethysmographic sensor and the piezoelectric pulse wave sensor are disposed on a contact surface of the pulse transmission time measuring apparatus that comes into contact with a wrist when the pulse transmission time measuring apparatus is attached to the body, and
the piezoelectric pulse wave sensor detects the piezoelectric pulse wave signal corresponding to flow of blood in a radial artery.

23. The pulse transmission time measuring apparatus according to claim 22, wherein the piezoelectric pulse wave sensor is disposed on the contact surface such that when the pulse transmission time measuring apparatus is attached to the body, the piezoelectric pulse wave sensor comes into contact with an area of an epidermis over the radial artery.

24. The pulse transmission time measuring apparatus according to claim 19, wherein an area of the contact surface where the piezoelectric pulse wave sensor is disposed has a shape that, when the pulse transmission time measuring apparatus is attached to the body, protrudes in a convex manner toward a wrist relative to an area of the contact surface where the piezoelectric pulse wave sensor is not disposed.

* * * * *